(12) United States Patent
Milne et al.

(10) Patent No.: US 9,216,224 B2
(45) Date of Patent: Dec. 22, 2015

(54) FATTY ACID COX INHIBITOR DERIVATIVES AND THEIR USES

(75) Inventors: Jill C. Milne, Brookline, MA (US); Michael R. Jirousek, Cambridge, MA (US); Jean E. Bemis, Arlington, MA (US); Chi B. Vu, Arlington, MA (US)

(73) Assignee: Catabasis Pharmaceuticals, Inc., Cambridge, MA (US)

( * ) Notice: Subject to any disclaimer, the term of this patent is extended or adjusted under 35 U.S.C. 154(b) by 18 days.

(21) Appl. No.: 13/582,932

(22) PCT Filed: Mar. 4, 2011

(86) PCT No.: PCT/US2011/027133
§ 371 (c)(1),
(2), (4) Date: Nov. 12, 2012

(87) PCT Pub. No.: WO2011/109681
PCT Pub. Date: Sep. 9, 2011

(65) Prior Publication Data
US 2013/0065934 A1    Mar. 14, 2013

Related U.S. Application Data

(60) Provisional application No. 61/310,947, filed on Mar. 5, 2010.

(51) Int. Cl.
*A61K 47/48*    (2006.01)

(52) U.S. Cl.
CPC ......... *A61K 47/48038* (2013.01); *A61K 47/481* (2013.01)

(58) Field of Classification Search
CPC ....................... A61K 47/481; A61K 47/48038
See application file for complete search history.

(56) References Cited

FOREIGN PATENT DOCUMENTS

| | | |
|---|---|---|
| EP | 0675103 | 10/1995 |
| WO | WO 96/34846 | 11/1996 |
| WO | WO 96/34855 | 11/1996 |
| WO | WO 98/18751 | 5/1998 |
| WO | WO 02/089787 | 11/2002 |
| WO | WO 2009/148698 | 12/2009 |
| WO | WO 2010/006085 | 1/2010 |

OTHER PUBLICATIONS

Vardar-Sengul, et al. J. Periodontol 2008, vol. 79, No. 10, p. 1934.*
Vippagunta, et al. Advanced Drug Delivery Reviews 48 (2001) 3-26.*
Horrobin, et al. Document No. 124:156001, retrieved from CAPLUS; 1995.*
Lee, et al. International Journal of Pharmaceutics 372 (2009) 112-124.*
Yu, et al. Document No. 160:53635, retrieved from CAPLUS; 2009.*
Sozio, et al. Arch. Pharm. Chem. Life Sci. (2010), 133-142.*
International Search Report and Written Opinion for PCT/US2011/027133, mailed Jul. 22, 2011, 8 pages.
Lovell, M. A. et al., "Protection against amyloid beta peptide and iron/hydrogen peroxide toxicity by alpha lipoic acid," Journal of Alzheimers' Disease, 5(3):229-239 (2003).
Rao, P. N. et al., "Evolution of Nonsteroidal Anti-Inflammatory Drugs (NSAIDs): Cyclooxygenase (COX) Inhibition and Beyond," J. Pharm. Pharmaceut. Sci., 11(2):81S-110S (2008).
Sozio, P. et al., "Ibuprofen and lipoic acid diamides as potential codrugs with neuroprotective activity," Arch. Pharm. Chem. Life Sci., 343(3):133-142 (2010).
Weggen, S. et al., "A subset of NSAIDs lower amyloidogenic Aβ42 independently of cyclooxygenase activity," Nature, 414:212-216 (2001).
McKee, A. C. et al., "Ibuprofen reduces Aβ, hyperphosphorylated tau and memory deficits in Alzheimer mice," Brain Res., 1207:225-236 (2008).
Vlad, S. et al., "Protective effects of NSAIDs on the development of Alzheimer disease," Neurology, 70(19):1672-1677 (2008).

* cited by examiner

*Primary Examiner* — Shawquia Jackson
(74) *Attorney, Agent, or Firm* — Goodwin Procter LLP

(57) ABSTRACT

The invention relates to fatty acid COX inhibitor derivatives; compositions comprising an effective amount of a fatty acid COX inhibitor derivative; and methods for treating or preventing a metabolic, autoimmune, inflammatory, or neurodegenerative disorder comprising the administration of an effective amount of a fatty acid COX inhibitor derivative.

27 Claims, No Drawings

US 9,216,224 B2

FATTY ACID COX INHIBITOR DERIVATIVES AND THEIR USES

PRIORITY

The present application claims the benefit of U.S. Provisional Application No. 61/310,947 filed Mar. 5, 2010, the entire disclosure of which is relied on for all purposes and is incorporated into this application by reference.

FIELD OF THE INVENTION

The invention relates to fatty acid COX inhibitor derivatives; compositions comprising an effective amount of a fatty acid COX inhibitor derivative; and methods for treating or preventing a metabolic, autoimmune, inflammatory, or neurodegenerative disorder comprising the administration of an effective amount of a fatty acid COX inhibitor derivative. All patents, patent applications, and publications cited herein are hereby incorporated by reference in their entireties.

BACKGROUND OF THE INVENTION

Oily cold water fish, such as salmon, trout, herring, and tuna are the source of dietary marine omega-3 fatty acids, with eicosapentaenoic acid (EPA) and docosahexaenoic acid (DHA) being the key marine derived omega-3 fatty acids. Omega-3 fatty acids have previously been shown to improve insulin sensitivity and glucose tolerance in normoglycemic men and in obese individuals. Omega-3 fatty acids have also been shown to improve insulin resistance in obese and non-obese patients with an inflammatory phenotype. Lipid, glucose, and insulin metabolism have been shown to improve in overweight hypertensive subjects through treatment with omega-3 fatty acids. Omega-3 fatty acids (EPA/DHA) have also been shown to decrease triglycerides and to reduce the risk for sudden death caused by cardiac arrhythmias in addition to improve mortality in patients at risk of a cardiovascular event. Omega-3 fatty acids have also been taken as part of the dietary supplement portion of therapy used to treat dyslipidemia. Last, but not least, omega-3 fatty acids have been known to have a number of anti-inflammatory properties. For instance, a higher intake of omega-3 fatty acids lower levels of circulating TNF-α and IL-6, two of the cytokines that are markedly increased during inflammation processes (Chapkin et al, *Prostaglandins, Leukot Essent Fatty Acids* 2009, 81, p. 187-191; Duda et al, *Cardiovasc Res* 2009, 84, p. 33-41). In addition, a higher intake of omega-3 fatty acids has been shown to increase levels of the well-characterized anti-inflammatory cytokine IL-10 (Bradley et al, *Obesity (Silver Spring)* 2008, 16, p. 938-944). More recently, administration of omega-3 fatty acids could protect against pathologic retinal angiogenesis in a mouse model of oxygen-induced retinopathy (K. M. Connor et al, *Nat. Med.* 2007, 13, p. 868-873; P. Sapieha et al *Science Translational Medicine* 2011, 3, issue 69, p. 1-12). Because of this anti-angiogenic property, omega-3 fatty acids could potentially be used as an anti-VEGF (vascular endothelial growth factor) therapy for the treatment of proliferative retinopathy or systemic diseases with perturbed vascular growth such as cancer.

Both DHA and EPA are characterized as long chain fatty acids (aliphatic portion between 12-22 carbons). Medium chain fatty acids are characterized as those having the aliphatic portion between 6-12 carbons. Lipoic acid is a medium chain fatty acid found naturally in the body. It plays many important roles such as free radical scavenger, chelator to heavy metals and signal transduction mediator in various inflammatory and metabolic pathways, including the NF-κB pathway (Shay, K. P. et al. *Biochim. Biophys. Acta* 2009, 1790, 1149-1160). Lipoic acid has been found to be useful in a number of chronic diseases that are associated with oxidative stress (for a review see Smith, A. R. et al *Curr. Med. Chem.* 2004, 11, p. 1135-46). Lipoic acid has now been evaluated in the clinic for the treatment of diabetes (Morcos, M. et al *Diabetes Res. Clin. Pract.* 2001, 52, p. 175-183) and diabetic neuropathy (Mijnhout, G. S. et al *Neth. J. Med.* 2010, 110, p. 158-162). Lipoic acid has also been found to be potentially useful in treating cardiovascular diseases (Ghibu, S. et al, *J. Cardiovasc. Pharmacol.* 2009, 54, p. 391-8), Alzheimer's disease (Maczurek, A. et al, *Adv. Drug Deliv. Rev.* 2008, 60, p. 1463-70) and multiple sclerosis (Yadav, V. *Multiple Sclerosis* 2005, 11, p. 159-65; Salinthone, S. et al, *Endocr. Metab. Immune Disord. Drug Targets* 2008, 8, p. 132-42).

COX inhibitors are non-steroidal anti-inflammatory agents which act as inhibitors of cyclooxygenase (COX). COX converts arachidonic acid to prostaglandin H2, which is subsequently converted to the prostaglandins, potent mediators of inflammation. COX inhibitors inhibit multiple isoforms of the cyclooxygenase enzyme. Inhibition of COX-2 imparts the anti-inflammatory and analgesic properties of COX inhibitors while the inhibition of COX-1 is responsible for the unwanted effects on platelet aggregation and the gastrointestinal tract (Rao, P.; Knaus, E. E. *J. Pharm. Sci.* 2008, 11 (2), 81S-110S). More recently, there have been reports that showed the potential benefits of administering non-steroidal anti-inflammatory drugs, along with an antioxidant, can protect against the development of Alzheimer's disease (P. Sozio et al, *Arch. Pharm. Chem. Life Sci.* 2010, 343, p. 133-142; M. A. Lovell et al *J. Alzheimers' Disease* 2003, 5, p. 229-239). In particular, ibuprofen and indomethacin are two of the COX inhibitors that have been shown to have a positive impact on the production of amyloid β peptide in cell cultures (S. Weggen et al *Nature* 2001, 414, p. 212-216; S. Vlad et al, *Neurology* 2008, 70, p. 1672-1677; A. McKee *Brain Res.* 2008; 1207, p. 225-236). Fatty acid COX inhibitor derivatives are inactive against the COX enzyme until they enter the cell and are hydrolyzed into the individual components to produce free COX inhibitor and free fatty acid. Thus, the side effects of COX inhibitors, including stomach ulcer and gastrointestinal distress, are minimized.

The ability to provide the effects of COX inhibitors and fatty acids in a synergistic way would provide benefits in treating a variety of metabolic, autoimmune and inflammatory disorders.

SUMMARY OF THE INVENTION

The invention is based in part on the discovery of fatty acid COX inhibitor derivatives and their demonstrated effects in achieving improved treatment that cannot be achieved by administering fatty acids or COX inhibitors, alone, or in simple (non covalently linked) combination. These novel compounds are useful to relieve the inflammation, swelling, stiffness, and joint pain associated with rheumatoid arthritis, osteoarthritis, juvenile arthritis, ankylosing spondylitis, tendinitis, bursitis, and acute gout. In addition, they are used to treat pain associates with menstrual periods, migraine headaches, dental pain, and other types of mild to moderate pain.

Accordingly in one aspect, a molecular conjugate is described which comprises a COX inhibitor and a fatty acid covalently linked, wherein the fatty acid is selected from the group consisting of omega-3 fatty acids, fatty acids that are metabolized in vivo to omega-3 fatty acids, and lipoic acid, and the conjugate is capable of hydrolysis to produce free COX inhibitor and free fatty acid, with the proviso, that the molecular conjugate is not (5Z,8Z,11Z,14Z,17Z)-1-(2-(1-(4-chlorobenzoyl)-5-methoxy-2-methyl-1H-indol-3-yl)acetoxy)ethyl icosa-5,8,11,14,17-pentaenoate or 5-((S)-1,2-dithiolan-3-yl)-N-(2-(2-(4-isobutylphenyl)propanamido)ethyl)pentanamide. In some embodiments, the fatty acid is selected from the group consisting of all-cis-7,10,13-hexadecatrienoic acid, α-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid, tetracosahexaenoic acid and lipoic acid. In other embodiments, the fatty acid is selected from eicosapentaenoic acid, docosahexaenoic acid and lipoic acid. In some embodiments, the COX inhibitor is selected from the group consisting of propionic acid derivatives such as but not limited to ibuprofen, naproxen, fenoprofen, ketoprofen, flurbiprofen, and oxaprozin, acetic acid derivatives such as but not limited to indomethacin, sulindac, etodolac, and diclofenac, enolic acid/oxicam derivatives such as but not limited to piroxicam, meloxicam, tenoxicam, droxicam, lornoxicam, and isoxicam, and fenamic acid derivatives such as but not limited to mefenamic acid, meclofenamic acid, flufenamic acid, and tolfenamic acid. In some embodiments, the hydrolysis is enzymatic. Fatty acid COX inhibitor derivatives are inactive against the COX enzyme until they enter the cell and are hydrolyzed into the individual components to produce free COX inhibitor and free fatty acid. Thus, the side effects of COX inhibitors, including stomach ulcer and gastrointestinal distress, are minimized.

In another aspect, compounds of the Formula I are described:

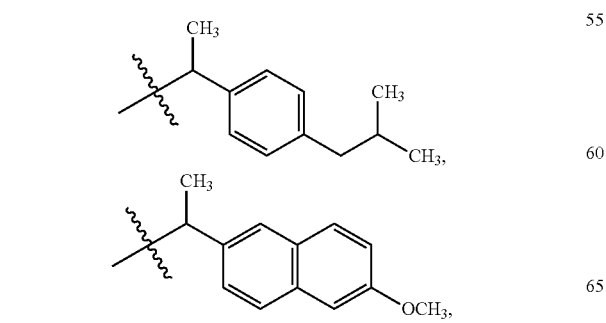

Formula I and pharmaceutically acceptable salts, hydrates, solvates, prodrugs, enantiomers, and stereoisomers thereof;
wherein
$R_n$ is

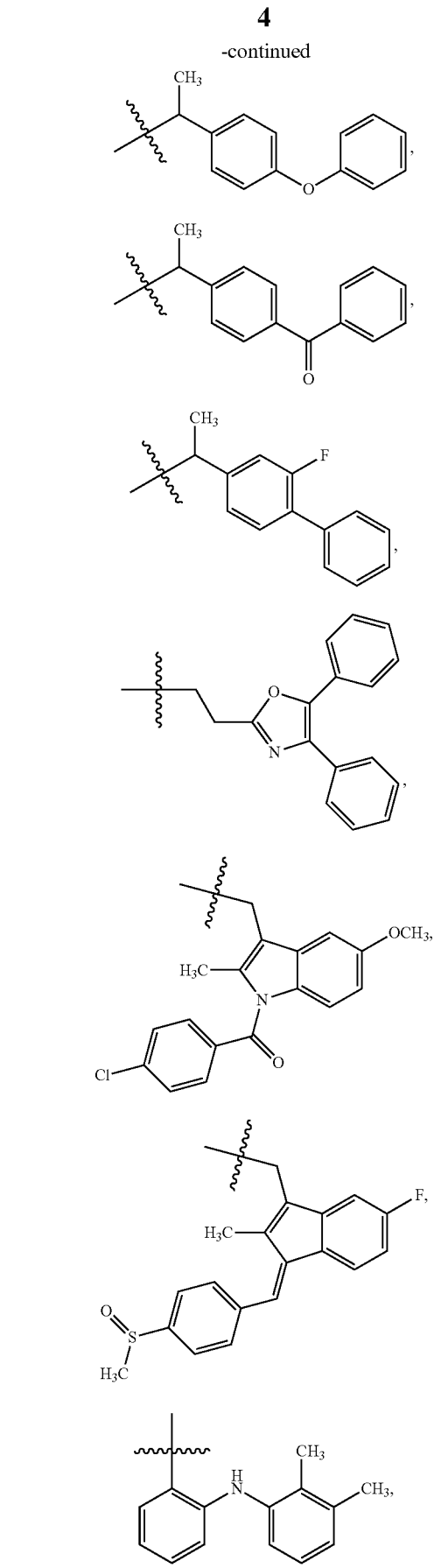

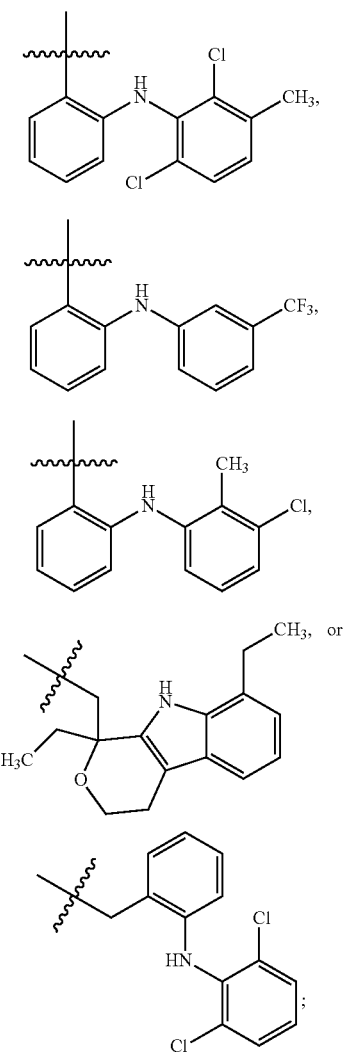

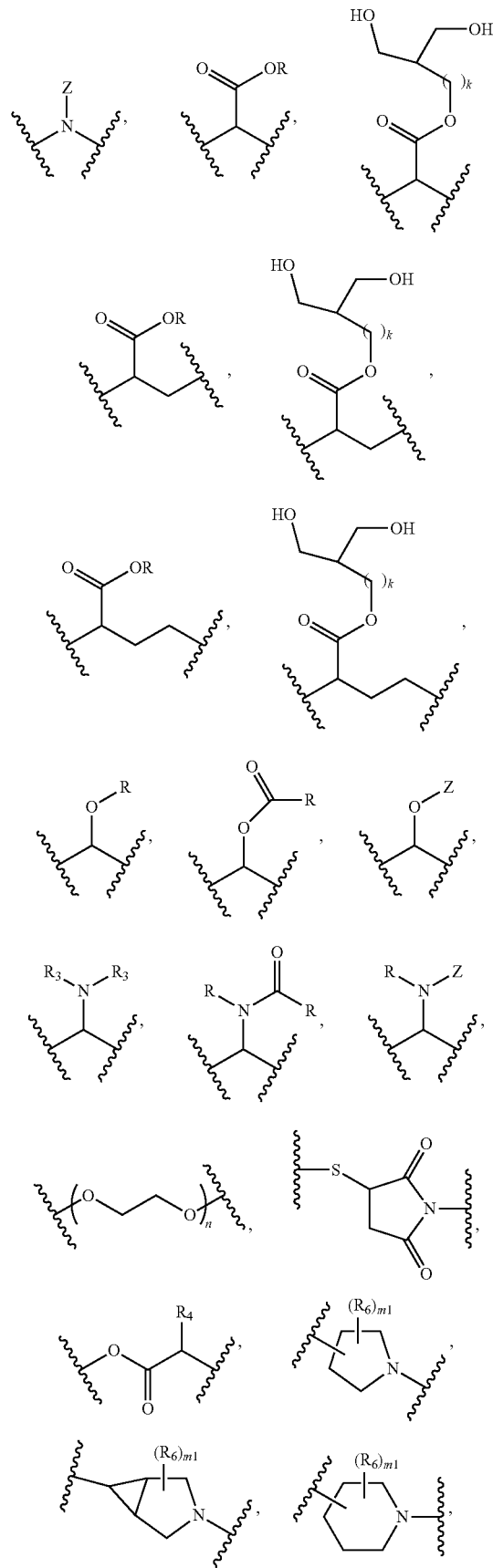

W₁ and W₂ are each independently null, O, S, NH, NR, or W₁ and W₂ can be taken together can form an imidazolidine or piperazine group, with the proviso that W₁ and W₂ can not be O simultaneously;

each a, b, c and d is independently —H, -D, —CH₃, —OCH₃, —OCH₂CH₃, —C(O)OR, or —O—Z, or benzyl, or two of a, b, c, and d can be taken together, along with the single carbon to which they are bound, to form a cycloalkyl or heterocycle;

each n, o, p, and q is independently 0, 1 or 2;

each L is independently null, —O—, —S—, —S(O)—, —S(O)₂—, —S—S—, —(C₁-C₆alkyl)-, —(C₃-C₆cycloalkyl)-, a heterocycle, a heteroaryl,

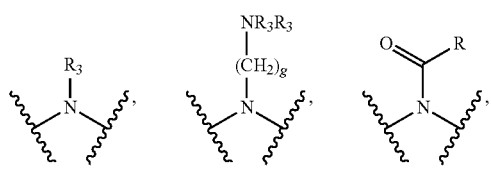

-continued

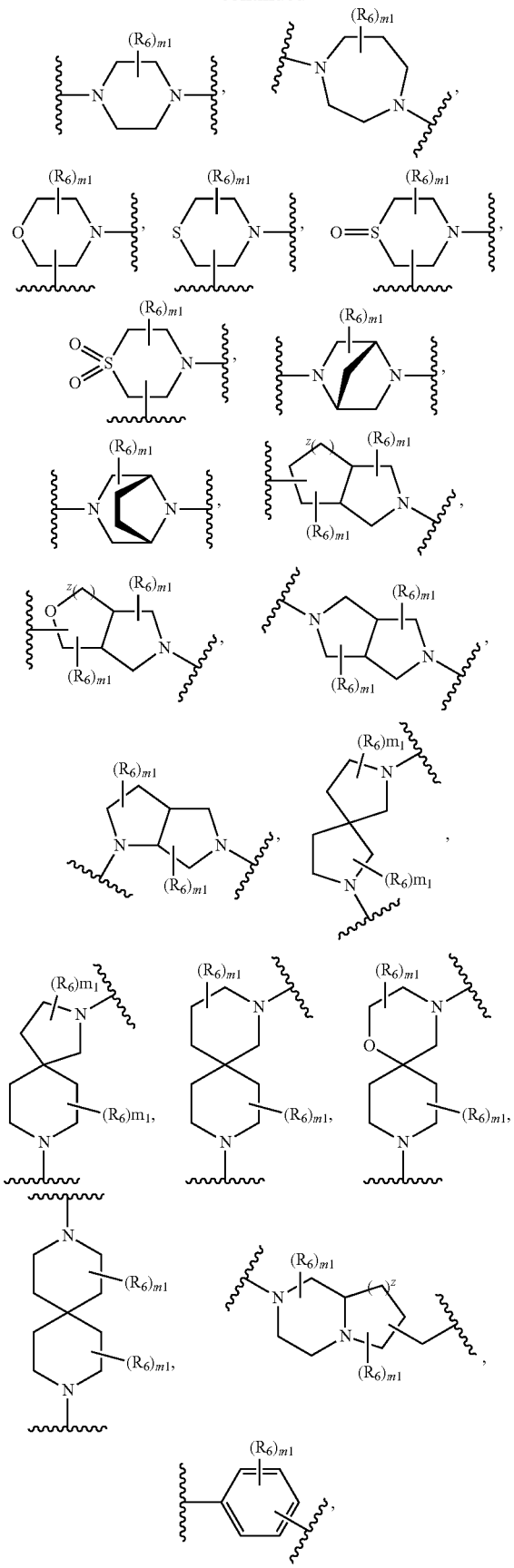

wherein the representation of L is not limited directionally left to right as is depicted, rather either the left side or the right side of L can be bound to the $W_1$ side of the compound of Formula I;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each g is independently 2, 3 or 4;
each h is independently 1, 2, 3 or 4;
m is 0, 1, 2, or 3; if m is more than 1, then L can be the same or different;
m1 is 0, 1, 2 or 3;
k is 0, 1, 2, or 3;
z is 1, 2, or 3;
each $R_3$ is independently H or $C_1$-$C_6$ alkyl, or both $R_3$ groups, when taken together with the nitrogen to which they are attached, can form a heterocycle;
each $R_4$ is independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;
each e is independently H or any one of the side chains of the naturally occurring amino acids;
each z is independently —H,

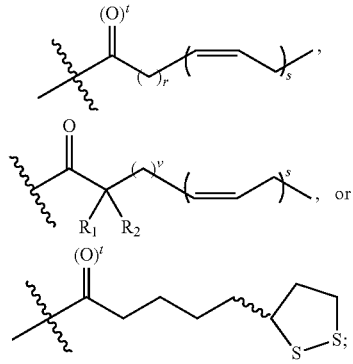

with the proviso that there is at least one

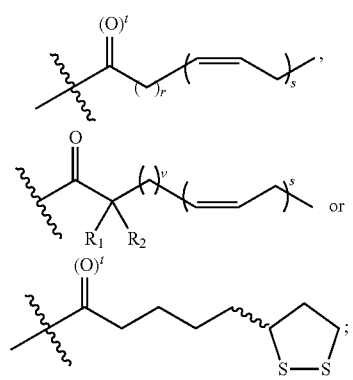

in the compound;
each r is independently 2, 3, or 7;
each s is independently 3, 5, or 6;

each t is independently 0 or 1;
each v is independently 1, 2, or 6;
$R_1$ and $R_2$ are each independently hydrogen, deuterium, $C_1$-$C_4$ alkyl, -halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and
each R is independently —H, —$C_1$-$C_3$ alkyl, or straight or branched $C_1$-$C_4$ alkyl optionally substituted with OH, or halogen;
provided that
when m, n, o, p, and q are each 0, $W_1$ and $W_2$ are each null, and Z is

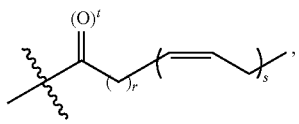

then t must be 0; and
when m, n, o, p, and q are each 0, and $W_1$ and $W_2$ are each null, then Z must not be

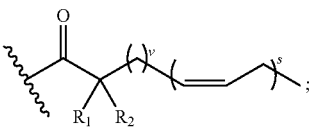

with the further proviso that the compound is not 5Z,8Z,11Z,14Z,17Z)-1-(2-(1-(4-chlorobenzoyl)-5-methoxy-2-methyl-1H-indol-3-yl)acetoxy)ethyl icosa-5,8,11,14,17-pentaenoate or 5-((S)-1,2-dithiolan-3-yl)-N-(2-(2-(4-isobutylphenyl)propanamido)ethyl)pentanamide.

In Formula I, any one or more of H may be substituted with a deuterium. It is also understood in Formula I, that a methyl substituent can be substituted with a $C_1$-$C_6$ alkyl.

Also described are pharmaceutical formulations comprising at least one fatty acid COX inhibitor derivative.

Also described herein are methods of treating a disease susceptible to treatment with a fatty acid COX inhibitor derivative in a patient in need thereof by administering to the patient an effective amount of a fatty acid COX inhibitor derivative.

Also described herein are methods of treating metabolic diseases or autoimmune disease or neurodegenerative diseases by administering to a patient in need thereof an effective amount of a fatty acid COX inhibitor derivative.

The invention also includes pharmaceutical compositions that comprise an effective amount of a fatty acid COX inhibitor derivative and a pharmaceutically acceptable carrier. The compositions are useful for treating or preventing a metabolic disease. The invention includes a fatty acid COX inhibitor derivative provided as a pharmaceutically acceptable prodrug, a hydrate, a salt, such as a pharmaceutically acceptable salt, enantiomer, stereoisomer, or mixtures thereof.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DETAILED DESCRIPTION OF THE INVENTION

The fatty acid COX inhibitor derivatives have been designed to bring together fatty acids and COX inhibitors into a single molecular conjugate. The activity of the fatty acid COX inhibitor derivatives is substantially greater than the sum of the individual components of the molecular conjugate, suggesting that the activity induced by the fatty acid COX inhibitor derivatives is synergistic.

Definitions

The following definitions are used in connection with the fatty acid COX inhibitor derivatives:

The term "fatty acid COX inhibitor derivatives" includes any and all possible isomers, stereoisomers, enantiomers, diastereomers tautomers, pharmaceutically acceptable salts, hydrates, solvates, and prodrugs of the fatty acid COX inhibitor derivatives described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

"$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl.

"$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl.

"$C_1$-$C_5$ alkyl" refers to a straight or branched chain saturated hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl. It is understood that any of the substitutable hydrogens on a cycloalkyl can be substituted with halogen, $C_1$-$C_3$ alkyl, hydroxyl, alkoxy and cyano groups.

The term "heterocycle" as used herein refers to a cyclic hydrocarbon containing 3-6 atoms wherein at least one of the atoms is an O, N, or S. Examples of heterocycles include, but are not limited, to, aziridine, oxirane, thiirane, azetidine, oxetane, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to a monocyclic or bicyclic ring structure having 5 to 12 ring atoms wherein one or more of the ring atoms is a heteroatom, e.g. N, O or S and wherein one or more rings of the bicyclic ring structure is aromatic. Some examples of heteroaryl are pyridyl, furyl, pyrrolyl, thienyl, thiazolyl, oxazolyl, imidazolyl, indolyl, tetrazolyl, benzofuryl, xanthenes and dihydroindole. It is understood that any of the substitutable hydrogens on a heteroaryl can be substituted with halogen, $C_1$-$C_3$ hydroxyl, alkoxy and cyano groups.

The term "any one of the side chains of the naturally occurring amino acids" as used herein means a side chain of any one of the following amino acids: Isoleucine, Alanine, Leucine, Asparagine, Lysine, Aspartate, Methionine, Cysteine, Phenylalanine, Glutamate, Threonine, Glutamine, Tryptophan, Glycine, Valine, Praline, Arginine, Serine, Histidine, and Tyrosine.

The term "fatty acid" as used herein means an omega-3 fatty acid and fatty acids that are metabolized in vivo to omega-3 fatty acids. Non-limiting examples of fatty acids are all-cis-7,10,13-hexadecatrienoic acid, α-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA or all-cis-5,8,11,14,17-eicosapentaenoic acid), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15,18,21-docosahexaenoic acid), or tetracosahexaenoic acid (nisinic acid or all-cis-6,9,12,15,18,21-tetracosenoic acid). In addition, the term "fatty acid" can also refer to medium chain fatty acids such as lipoic acid.

The term "COX inhibitor" as used herein means any of the class of compounds known as COX inhibitors, and any derivatives thereof, including but not limited to propionic acid derivatives (such as ibuprofen, naproxen, fenoprofen, ketoprofen, flurbiprofen, and oxaprozin), acetic acid derivatives (such as indomethacin, sulindac, etodolac, and diclofenac), enolic acid/oxicam derivatives (such as piroxicam, meloxicam, tenoxicam, droxicam, lornoxicam, and isoxicam) and fenamic acid derivatives (such as mefenamic acid, meclofenamic acid, flufenamic acid, and tolfenamic acid).

A "subject" is a mammal, e.g., a human, mouse, rat, guinea pig, dog, cat, horse, cow, pig, or non-human primate, such as a monkey, chimpanzee, baboon or rhesus, and the terms "subject" and "patient" are used interchangeably herein.

The invention also includes pharmaceutical compositions comprising an effective amount of a fatty acid COX inhibitor derivative and a pharmaceutically acceptable carrier. The invention includes a fatty acid COX inhibitor derivative provided as a pharmaceutically acceptable prodrug, hydrate, salt, such as a pharmaceutically acceptable salt, enantiomers, stereoisomers, or mixtures thereof.

Representative "pharmaceutically acceptable salts" include, e.g., water-soluble and water-insoluble salts, such as the acetate, amsonate (4,4-diaminostilbene-2, 2-disulfonate), benzenesulfonate, benzoate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "metabolic disease" as used herein refers to disorders, diseases and syndromes involving dyslipidemia, and the terms metabolic disorder, metabolic disease, and metabolic syndrome are used interchangeably herein.

An "effective amount" when used in connection with a fatty acid COX inhibitor derivative is an amount effective for treating or preventing a metabolic disease.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating", with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a fatty acid COX inhibitor derivative.

The following abbreviations are used herein and have the indicated definitions: Boc and BOC are tert-butoxycarbonyl, $Boc_2O$ is di-tert-butyl dicarbonate, CDI is 1,1'-carbonyldiimidazole, DCC is N,N'-dicyclohexylcarbodiimide, DIEA is N,N-diisopropylethylamine, DMAP is 4-dimethylaminopyridine, DOSS is sodium dioctyl sulfosuccinate, EDC and EDCI are 1-ethyl-3-(3-dimethylaminopropyl)carbodiimide hydrochloride, EtOAc is ethyl acetate, h is hour, HATU is 2-(7-aza-1H-benzotriazole-1-yl)-1,1,3,3-tetramethyluronium hexafluorophosphate, HPMC is hydroxypropyl methylcellulose, min is minutes, Pd/C is palladium on carbon, TFA is trifluoroacetic acid, TGPS is tocopherol propylene glycol succinate, THF is tetrahydrofuran, and TNF is tumor necrosis factor.

Compounds

Accordingly in one aspect, a molecular conjugate is described which comprises a COX inhibitor and a fatty acid directly or indirectly covalently linked, wherein the fatty acid is selected from the group consisting of omega-3 fatty acids, fatty acids that are metabolized in vivo to omega-3 fatty acids, and lipoic acid, and the conjugate is capable of hydrolysis to produce free COX inhibitor and free fatty acid, with the proviso that the molecular conjugate is not (5Z,8Z,11Z,14Z, 17Z)-1-(2-(1-(4-chlorobenzoyl)-5-methoxy-2-methyl-1H-indol-3-yl)acetoxy)ethyl icosa-5,8,11,14,17-pentaenoate or 5-((S)-1,2-dithiolan-3-yl)-N-(2-(2-(4-isobutylphenyl)propanamido)ethyl)-pentanamide.

In some embodiments, the COX inhibitor is selected from the group consisting of propionic acid derivatives, acetic acid derivatives, and fenamic acid derivatives. In other embodiments, the COX inhibitor is selected from the group consisting of ibuprofen, 2-(6-methoxynaphthalen-2-yl)propanoic acid, fenoprofen, ketoprofen, flurbiprofen, oxaprozin, indomethacin, etodolac, diclofenac, mefanamic acid, flufenamic acid, meclofenamic acid, and tolfenamic acid. In other embodiments, the COX inhibitor is selected from the group consisting of ibuprofen, 2-(6-methoxynaphthalen-2-yl)propanoic acid, and indomethacin.

In some embodiments, the fatty acid is selected from the group consisting of all-cis-7,10,13-hexadecatrienoic acid, α-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid, tetraeosahexaenoic acid, and lipoic acid. In other embodiments, the fatty acid is selected from eicosapentaenoic acid and docosahexaenoic acid. In some embodiments, the hydrolysis is enzymatic.

In another aspect, the present invention provides fatty acid COX inhibitor derivatives according to Formula I:

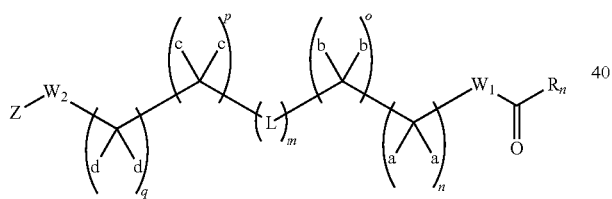

Formula I and pharmaceutically acceptable salts, hydrates, solvates, prodrugs, enantiomers and stereoisomers thereof;

wherein $W_1$, $W_2$, a, c, b, d, e, k, m, m1, n, o, p, q, L, Z, Z', r, s, t, v, z, $R_1$, $R_2$, $R_3$, $R_4$, R and $R_6$ are as defined above for Formula I, with the proviso that there is at least one of

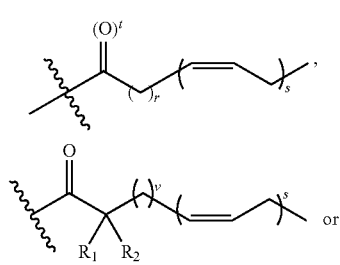

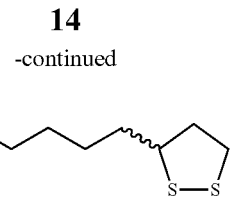

in the compound;

with the additional proviso that the compound is not (5Z, 8Z,11Z,14Z,17Z)-1-(2-(1-(4-chlorobenzoyl)-5-methoxy-2-methyl-1H-indol-3-yl)acetoxy)ethyl icosa-5,8,11,14,17-pentaenoate or 5-((S)-1,2-dithiolan-3-yl)-N-(2-(2-(4-isobutylphenyl)propanamido)ethyl)pentanamide.

In some embodiments, one Z is

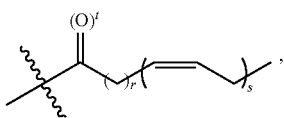

and r is 2.

In some embodiments, one Z is

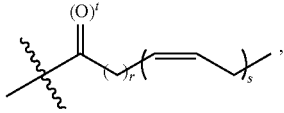

and r is 3.

In some embodiments, one Z is

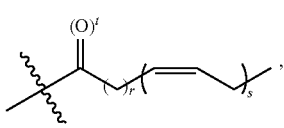

and r is 7.

In other embodiments, one Z is

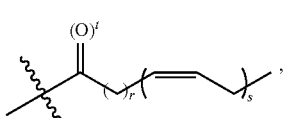

and s is 3.

In some embodiments, one Z is

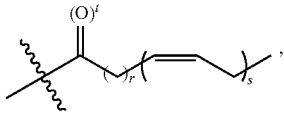

and s is 5.

In some embodiments, one Z is

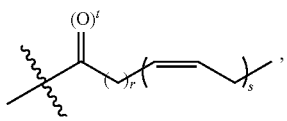

and s is 6.

In some embodiments, one Z is

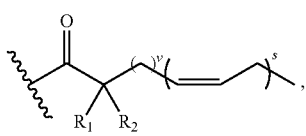

and v is 1.

In other embodiments, one Z is

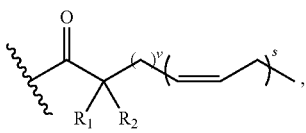

and v is 2.

In some embodiments, one Z is

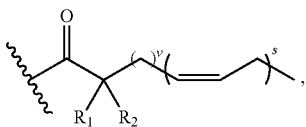

and v is 6.

In some embodiments, one Z is

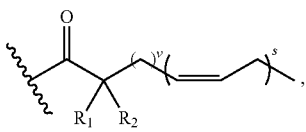

and s is 3.

In some embodiments, one Z is

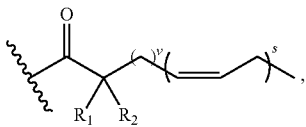

and s is 5.

In other embodiments, one Z is

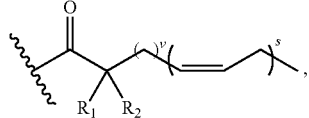

and s is 6.

In other embodiments, Z is

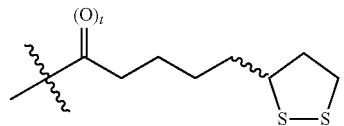

and t is 1.

In some embodiments, Z is

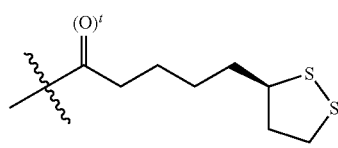

and t is 1.
In some embodiments, W1 is NH.
In some embodiments, W2 is NH.
In some embodiments, W1 is O.
In some embodiments, W2 is O.
In some embodiments, W1 is null.
In some embodiments, W2 is null.
In some embodiments, W1 and W2 are each NH.
In some embodiments, W1 and W2 are each null.
In some embodiments, W1 is O and W2 is NH.
In some embodiments, W1 and W2 are each NR, and R is CH3.
In some embodiments, m is 0.
In other embodiments, m is 1.
In other embodiments, m is 2.
In some embodiments, L is —S— or —S—S—.
In some embodiments, L is —O—.
In some embodiments, L is —C(O)—.
In some embodiments, L is heteroaryl.
In some embodiments, L is heterocycle.
In some embodiments, L is

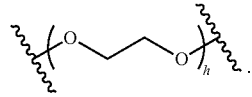

In some embodiments, L is

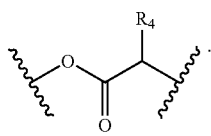

In some embodiments, L is
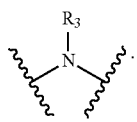
In some embodiments, L is
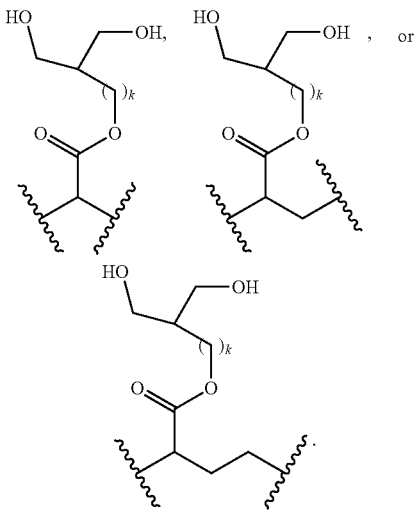
In some embodiments, L is
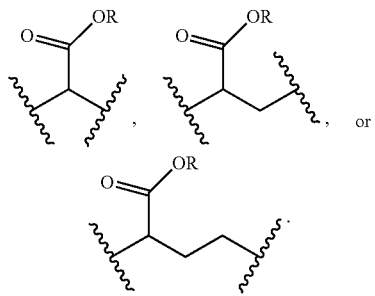
In some embodiments, L is
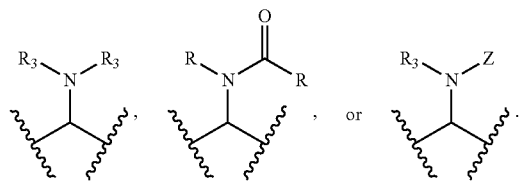
In some embodiments, L is
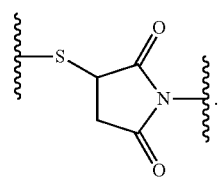
In some embodiments, L is
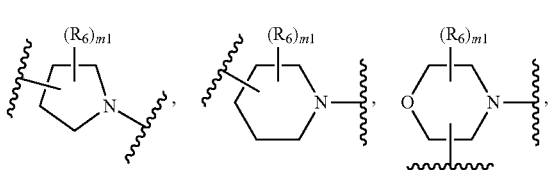
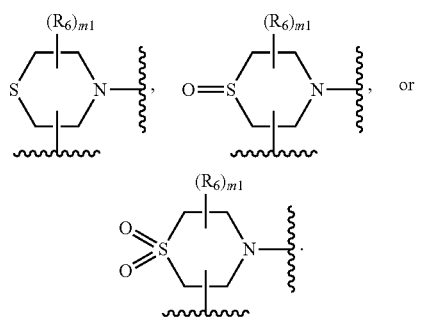
In some embodiments, L is
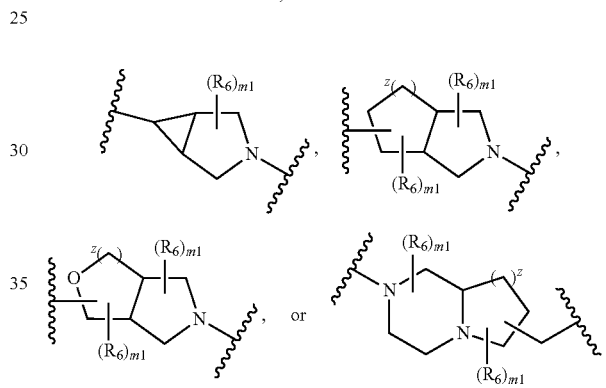
In some embodiments, L is
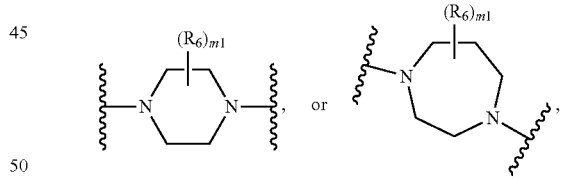
In some embodiments, L is
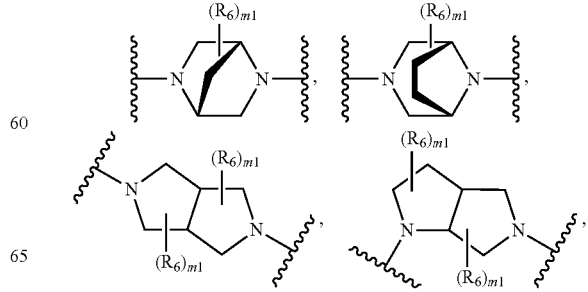

-continued

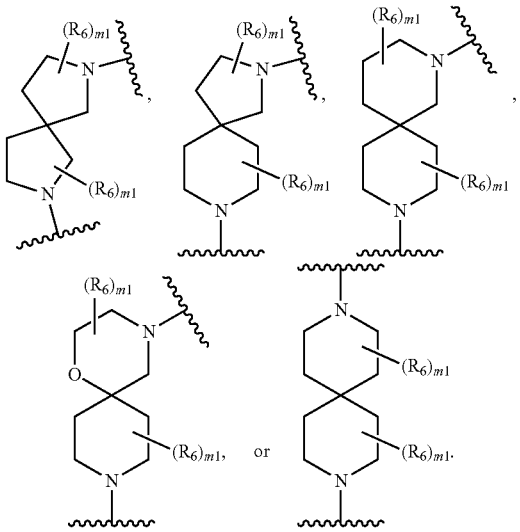

In other embodiments, one of n, o, p, and q is 1.
In some embodiments, two of n, o, p, and q are each 1.
In other embodiments, three of n, o, p, and q are each 1.
In some embodiments n, o, p, and q are each 1.
In some embodiments, one d is C(O)OR.
In some embodiments, r is 2 and s is 6.
In some embodiments, r is 3 and s is 5.
In some embodiments, t is 1.
In some embodiments, W1 and W2 are each NH, m is 0, n, and o are each 1, and p and q are each 0.
In some embodiments, W1 and W2 are each NH, m is 1, n, o, p, and q are each 1, and L is O.
In some embodiments, $W_1$ and $W_2$ are each NH, m is 1, n, o, p, and q are each 1, and L is

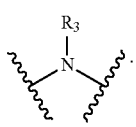

In some embodiments, $W_1$ and $W_2$ are each NH, m is 1, n, o, p, and q are each 1, and L is —S—S—.
In some embodiments, $W_1$ and $W_2$ are each NH, m is 1, n and o are each 0, p and q are each 1, and L is

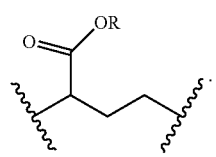

In some embodiments, $W_1$ and $W_2$ are each NH, m is 1, k is 0, n and o are each 0, p and q are each 1, and L is

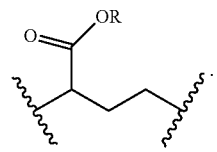

In some embodiments, $W_1$ and $W_2$ are each NH, m is 1, n and o are each 1, p and q are each 0, and L is

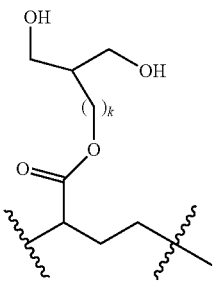

In some embodiments, $W_1$ and $W_2$ are each NH, m is 1, k is 0, n is 1, o, p and q are each 0, and L is

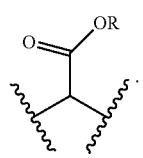

In some embodiments, $W_1$ and $W_2$ are each NH, m is 1, n, o, and p are each 0, and q is 1, and L is

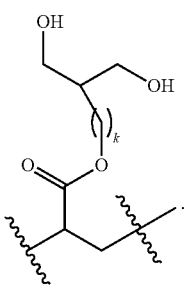

In some embodiments, $W_1$ and $W_2$ are each NH, m is 1, k is 1, n, o, and p are each 0, and q is 1, and L is In some embodiments, $W_1$ and $W_2$ are each NH, m is 1, n is 1, and o, p, and q are each 0, and L is

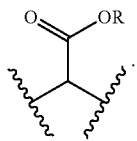

In some embodiments, $W_1$ and $W_2$ are each NH, m is 1, k is 1, o, p, and q are each 0, and L is

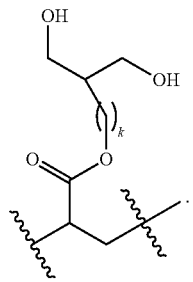

In some embodiments, $W_1$ and $W_2$ are each NH, m is 1, n, o, p, and q are each 1, and L is

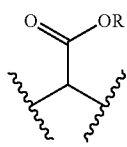

In some embodiments, $W_1$ and $W_2$ are each NH, m is 1, n, o, p, and q are each 1, and L is

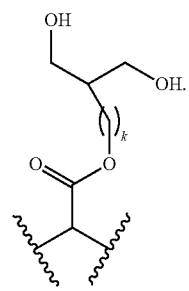

In some embodiments, W1 and W2 are each NH, m is 0, k is 1, o and p are each 1, and q is 0.

In some embodiments, W1 and W2 are each NH, m is 0, n, o, p, and q are each 1.

In some embodiments, W1 and W2 are each NH, m is 0, n and o are each 1, p and q are each 0, and each a is CH3.

In some embodiments, W1 and W2 are each NH, m is 0, n and o are each 1, p and q are each 0, and each b is CH3.

In some embodiments, $W_1$ and $W_2$ are each NH, m is 1, n, o, p, and q are each 1, $R_3$ is H, and L is

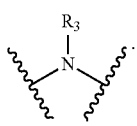

In some embodiments, $W_1$ and $W_2$ are each NH, m is 1, n, p and q are each 1, and o is 2, $R_3$ is H, and L is

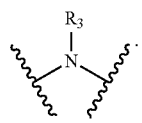

In some embodiments, $W_1$ and $W_2$ are each NH, m is 1, n, o, p are each 1, and q is 2, and L is

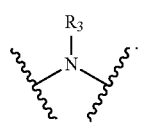

In some embodiments, $W_1$ and $W_2$ are each NH, m is 1, n, o, p, and q are each 1, and L is

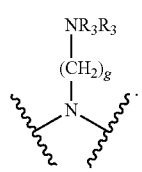

In some embodiments, W1 and W2 are each NH, m is 1, n and p are each 1, and o and q are each 0, and L is —C(O)—.

In some embodiments, W1 and W2 are each NH, m is 1, n and p are each 1, and o, and q are each 0, and L is

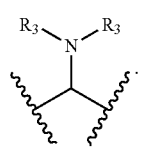

In some embodiments, $W_1$ and $W_2$ are each NH, m is 1, n, o, p, q are each 1, and L is

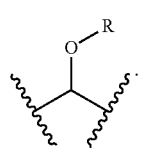

In some embodiments, $W_1$ and $W_2$ are each NH, m is 1, n, o, p and q are each 1, h is 1, and L is

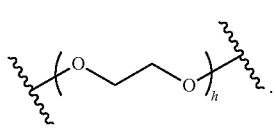

In some embodiments, $W_1$ and $W_2$ are each NH, m is 1, n, o, p, and q are each 1, and L is —S—.

In some embodiments, W1 and W2 are each NH, m is 1, n o, p are each 0, q is 1, one d is —CH$_3$, and L is

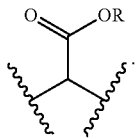

In some embodiments, W$_1$ and W$_2$ are each NH, m is 2, n, o, p, and q are each 0, one L is

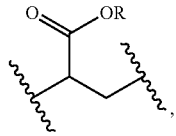

and
one L is

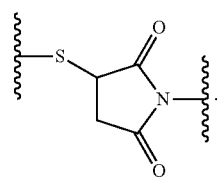 [SMILES: *SC1CC(=O)N(*)C1=O ; "."]

In some embodiments, m is 0, n, o, p, and q are each 0, and W1 and W2 are taken together to form an optionally substituted piperazine group.

In some embodiments, m is 1, n, o, p, and q are each 0, W1 and W2 are each null, and L is

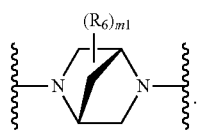

In some embodiments, m is 1, n and p are each 1, o and q are each 0, W$_1$ and W$_2$ are each NH, and L is C$_3$-C$_6$ cycloalkyl.

In some embodiments, m is 1, n is 1, o, p, and q are each 0, W$_1$ and W$_2$ are each NH, and L is C$_3$-C$_6$ cycloalkyl.

In some embodiments, m is 1, n, o, p, are each 0, q is 1, W$_1$ and W$_2$ are each NH, and L is C$_3$-C$_6$ cycloalkyl.

In some embodiments, m is 1, n, o, p, and q are each 0, W$_1$ is NH, W$_2$ is null, and L is

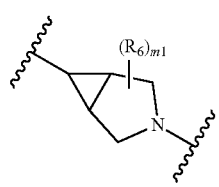

In some embodiments, m is 1, n o, p, and q are each 0, W$_1$ is null, W$_2$ is NH, and L is

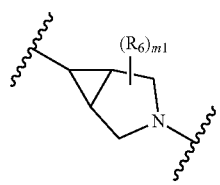

In some embodiments, m is 1, n o, p, and q are each 0, W1 is NH, W2 is null, and L is

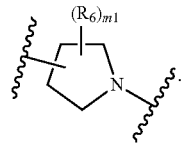

In some embodiments, m is 1, n o, p, and q are each 0, W$_1$ is null, W$_2$ is NH, and L is

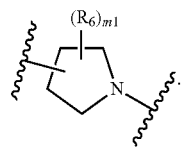

In some embodiments, m is 1, n is 1, o, p, and q are each 0, W1 is NH, W2 is null, and L is

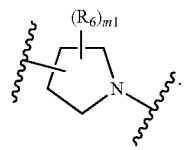

In some embodiments, m is 1, n, o, p, are each 0, q is 1, W$_1$ is null, W$_2$ is NH, and L is

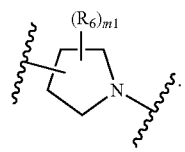

In some embodiments, m is 1, n, o, p, and q are each 0, W$_1$ is NH, W$_2$ is null, and L is

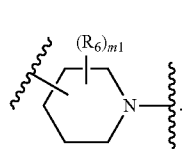

In some embodiments, m is 1, n, o, p, and q are each 0, W$_1$ is null, W$_2$ is NH, and L is

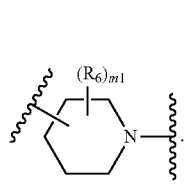

In some embodiments, m is 1, n is 1, o, p, and q are each 0, $W_1$ is NH, $W_2$ is null, and L is

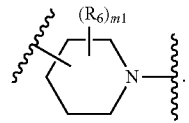

In some embodiments, m is 1, n, o, p, are each 0, q is 1, $W_1$ is null, $W_2$ is NH, and L is

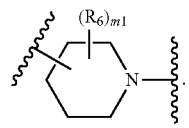

In some embodiments, m is 1, n is 1, o, p, and q are each 0, $W_1$ is NH, W2 is null, and L is

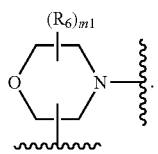

In some embodiments, m is 1, n, o, p, are each 0, q is 1, $W_1$ is null, $W_2$ is NH, and L is

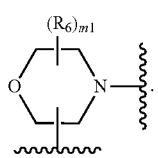

In some embodiments, m is 1, n, o, p, q are each 0, $W_1$ and $W_2$ is null, and L is

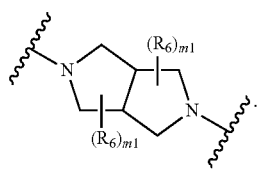

In some embodiments, m is 1, n, o, p, q are each 0, $W_1$ and $W_2$ is null, and L is

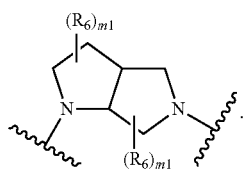

In some embodiments, m is 1, n, o, p, q are each 0, W1 is NH, $W_2$ is null, and L is

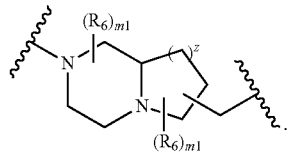

In some embodiments, m is 1, n, o, p, q are each 0, W1 is null, W2 is NH, and L is

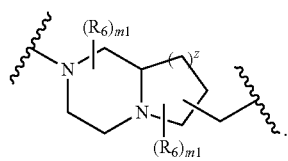

In some embodiments, m is 1, n, o, p, are each 0, q is 1, $W_1$ and $W_2$ are each and NH, is null, L is

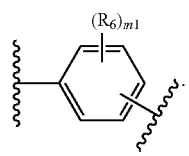

In some embodiments, m is 1, n, o, p, are each 0, q is 1, W1 and W2 are each NH, is null, and L is a heteroaryl.

In some of the foregoing embodiments, r is 2, s is 6 and t is 1.

In some of the foregoing embodiments, r is 3, s is 5 and t is 1.

In some of the foregoing embodiments, Z is

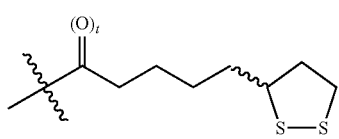

and
t is 1.

In some embodiments, $R_n$ is

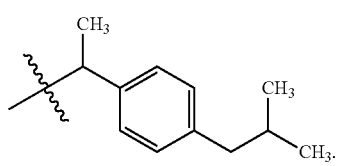 [SMILES: *C(C)c1ccc(CC(C)C)cc1]

In some embodiments, $R_n$ is

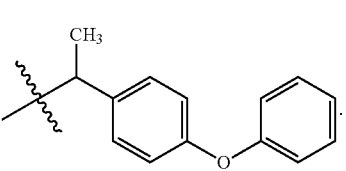 [SMILES: *C(C)c1ccc(Oc2ccccc2)cc1]

In some embodiments, $R_n$ is
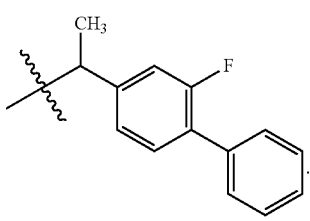 [SMILES: *C(C)c1ccc(-c2ccccc2)c(F)c1]
In some embodiments, $R_n$ is
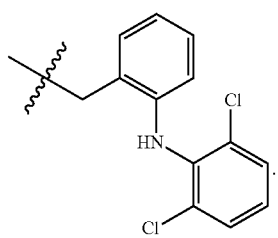 [SMILES: *Cc1ccccc1Nc1c(Cl)cccc1Cl]
In some embodiments, $R_n$ is
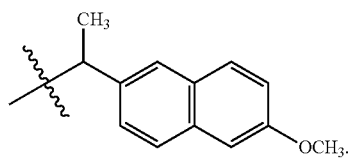 [SMILES: *C(C)c1ccc2cc(OC)ccc2c1]
In some embodiments, $R_n$ is
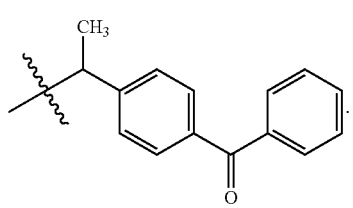 [SMILES: *C(C)c1ccc(C(=O)c2ccccc2)cc1]
In some embodiments, $R_n$ is
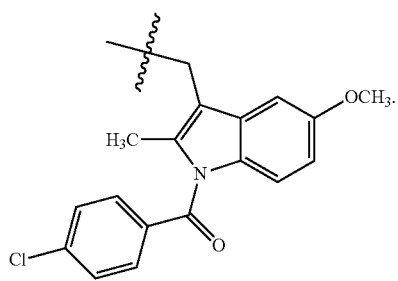 [SMILES: *Cc1c(C)n(C(=O)c2ccc(Cl)cc2)c2ccc(OC)cc12]
In some embodiments, $R_n$ is
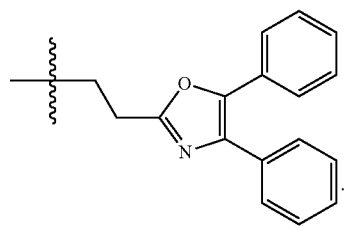 [SMILES: *CCc1nc(-c2ccccc2)c(-c2ccccc2)o1]
In some embodiments, $R_n$ is
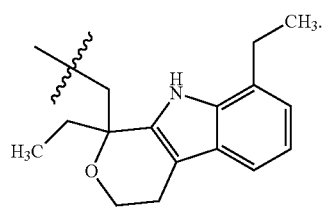 [SMILES: *CC1(CC)OCCc2c1[nH]c1c(CC)cccc21]
In some embodiments, $R_n$ is
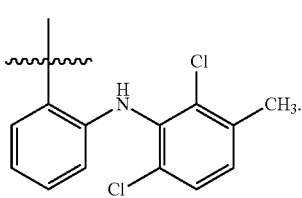 [SMILES: *c1ccccc1Nc1c(Cl)ccc(C)c1Cl]
In some embodiments, $R_n$ is
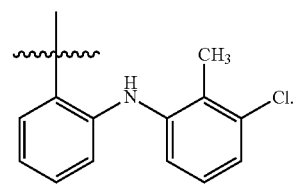 [SMILES: *c1ccccc1Nc1cccc(Cl)c1C]
In some embodiments, $R_n$ is
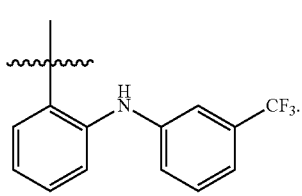 [SMILES: *c1ccccc1Nc1cccc(C(F)(F)F)c1]
In some embodiments, $R_n$ is
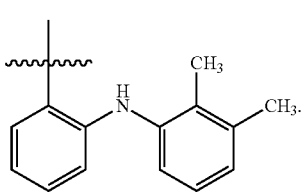 [SMILES: *c1ccccc1Nc1cccc(C)c1C]

In some embodiments, $R_n$ is

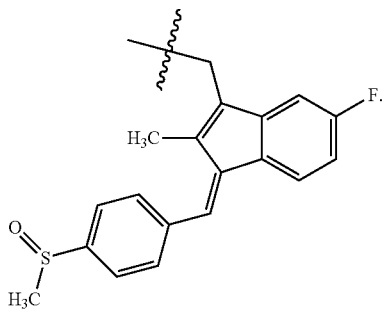

In Formula I, any one or more of H may be substituted with a deuterium. It is also understood in Formula I, that a methyl substituent can be substituted with a $C_1$-$C_6$ alkyl.

In other illustrative embodiments, compounds of Formula I are as set forth below:
(4Z,7Z,10Z,13Z,16Z,19Z)—N-(2-(2-(4-isobutylphenyl)propanamido)ethyl)docosa-4,7,10,13,16,19-hexaenamide (I-1);
(5Z,8Z,11Z,14Z,17Z)—N-(2-(2-(4-isobutylphenyl)propanamido)ethyl)icosa-5,8,11,14,17-pentaenamide (I-2);
(4Z,7Z,10Z,13Z,16Z,19Z)—N-(2-(2-(2-(4-isobutylphenyl)propanamido)ethoxy)ethyl)docosa-4,7,10,13,16,19-hexaenamide (I-3);
(4Z,7Z,10Z,13Z,16Z,19Z)—N-(2-((2-(2-(4-isobutylphenyl)propanamido)ethyl)(methyl)amino)ethyl)docosa-4,7,10,13,16,19-hexaenamide (I-4);
6-(4Z,7Z,10Z,13Z,16Z,19Z)-docosa-4,7,10,13,16,19-hexaenamido-2-(2-(4-isobutylphenyl)propanamido)hexanoic acid (II-5);
(S,4Z,7Z,10Z,13Z,16Z,19Z)—N-(2-(2-(6-methoxynaphthalen-2-yl)propanamido)ethyl)docosa-4,7,10,13,16,19-hexaenamide (I-6);
(S,5Z,8Z,11Z,14Z,17Z)—N-(2-(2-(6-methoxynaphthalen-2-yl)propanamido)ethyl)icosa-5,8,11,14,17-pentaenamide (I-7);
(S,4Z,7Z,10Z,13Z,16Z,19Z)—N-(2-(2-(2-(6-methoxynaphthalen-2-yl)propanamido)ethoxy)ethyl)docosa-4,7,10,13,16,19-hexaenamide (I-8);
(S,4Z,7Z,10Z,13Z,16Z,19Z)—N-(2-((2-(2-(6-methoxynaphthalen-2-yl)propanamido)ethyl)(methyl)amino)ethyl)docosa-4,7,10,13,16,19-hexaenamide (I-9);
6-(4Z,7Z,10Z,13Z,16Z,19Z)-docosa-4,7,10,13,16,19-hexaenamido-2-((S)-2-(6-methoxynaphthalen-2-yl)propanamido)hexanoic acid (I-10);
(4Z,7Z,10Z,13Z,16Z,19Z)—N-(2-(2-(1-(4-chlorobenzoyl)-5-methoxy-2-methyl-1H-indol-3-yl)acetamido)ethyl)docosa-4,7,10,13,16,19-hexaenamide (I-11);
(5Z,8Z,11Z,14Z,17Z)—N-(2-(2-(1-(4-chlorobenzoyl)-5-methoxy-2-methyl-1H-indol-3-yl)acetamido)ethyl)icosa-5,8,11,14,17-pentaenamide (I-12);
(4Z,7Z,10Z,13Z,16Z,19Z)—N-(2-(2-(2-(1-(4-chlorobenzoyl)-5-methoxy-2-methyl-1H-indol-3-yl)acetamido)ethoxy)ethyl)docosa-4,7,10,13,16,19-hexaenamide (I-13);
(4Z,7Z,10Z,13Z,16Z,19Z)—N-(2-((2-(2-(1-(4-chlorobenzoyl)-5-methoxy-2-methyl-1H-indol-3-yl)acetamido)ethyl)(methyl)amino)ethyl)docosa-4,7,10,13,16,19-hexaenamide (I-14);
(4Z,7Z,10Z,13Z,16Z,19Z)—N-(2-(2-(2-(2-(1-(4-chlorobenzoyl)-5-methoxy-2-methyl-1H-indol-3-yl)acetamido)ethyl)disulfanyl)ethyl)docosa-4,7,10,13,16,19-hexaenamide (I-15);
2-(2-(1-(4-chlorobenzoyl)-5-methoxy-2-methyl-1H-indol-3-yl)acetamido)-6-(4Z,7Z,10Z,13Z,16Z,19Z)-docosa-4,7,10,13,16,19-hexaenamidohexanoic acid (I-17);
(4Z,7Z,10Z,13Z,16Z,19Z)—N-(2-(2-(2-(3-phenoxyphenyl)propanamido)ethyl)disulfanyl)ethyl)docosa-4,7,10,13,16,19-hexaenamide (I-18);
(4Z,7Z,10Z,13Z,16Z,19Z)—N-(2-(2-(2-(2,6-dichlorophenylamino)phenyl)acetamido)ethyl)docosa-4,7,10,13,16,19-hexaenamide (I-19);
(4Z,7Z,10Z,13Z,16Z,19Z)—N-(2-(3-(4,5-diphenyloxazol-2-yl)propanamido)ethyl)docosa-4,7,10,13,16,19-hexaenamide (I-20);
(4Z,7Z,10Z,13Z,16Z,19Z)—N-(2-(2-(3-benzoylphenyl)propanamido)ethyl)docosa-4,7,10,13,16,19-hexaenamide (I-21);
(4Z,7Z,10Z,13Z,16Z,19Z)—N-(2-(2-(1,8-diethyl-1,3,4,9-tetrahydropyrano[3,4-b]indol-1-yl)acetamido)ethyl)docosa-4,7,10,13,16,19-hexaenamide (I-22);
2-(2,6-dichloro-3-methylphenylamino)-N-(2-(4Z,7Z,10Z,13Z,16Z,19Z)-docosa-4,7,10,13,16,19-hexaenamidoethyl)benzamide (I-23);
N-(2-(4Z,7Z,10Z,13Z,16Z,19Z)-docosa-4,7,10,13,16,19-hexaenamidoethyl)-2-(3-(trifluoromethyl)phenylamino)benzamide (I-24); and
2-(2,3-dimethylphenylamino)-N-(2-(4Z,7Z,10Z,13Z,16Z,19Z)-docosa-4,7,10,13,16,19-hexaenamidoethyl)benzamide (I-25).

Methods for Using Fatty Acid COX Inhibitor Derivatives

The invention also includes methods to relieve the inflammation, swelling, stiffness, and joint pain associated with rheumatoid arthritis, osteoarthritis, juvenile arthritis, ankylosing spondylitis, tendinitis, bursitis, and acute gout. In addition, it is used to treat pain associates with menstrual periods, migraine headaches, dental pain, and other types of mild to moderate pain. The compounds of this invention can also be used for treating or preventing the development of inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis.

Also provided in the invention is a method for inhibiting, preventing, or treating an inflammatory disorder, or symptoms of an inflammatory disease, in a subject. Examples of such disorders include, but are not limited to relieve the inflammation, swelling, stiffness, and joint pain associated with rheumatoid arthritis, osteoarthritis, juvenile arthritis, ankylosing spondylitis, tendinitis, bursitis, and acute gout. In addition, it is used to treat pain associates with menstrual periods, migraine headaches, dental pain, and other types of mild to moderate pain.

Furthermore, because of the potential anti-angiogenic property, the compounds of this invention can potentially be used as an anti-VEGF (vascular endothelial growth factor) therapy for the treatment of proliferative retinopathy or systemic diseases with perturbed vascular growth such as cancer.

Examples of eye-related diseases in which anti-VEGF therapy has been found to be effective include wet age-related macular degeneration, central retinal vein occlusion and diabetic macular edema. The compounds described herein are also useful in treating a variety of cancer such as carcinoma, sarcoma, lymphoma, leukemia, melanoma, mesothelioma, multiple myeloma, seminoma, and cancer of the bladder, blood, bone, brain, breast, central nervous system, colon, endometrium, esophagus, genitourinary tract, head, larynx, liver, lung, neck, ovary, pancreas, prostate, testicle, spleen, small intestine, large intestine or stomach.

The invention also includes pharmaceutical compositions useful for treating or preventing a metabolic disease, or for inhibiting a metabolic disease, or more than one of these activities. The compositions can be suitable for internal use and comprise an effective amount of a fatty acid COX inhibitor derivative and a pharmaceutically acceptable carrier. The fatty acid COX inhibitor derivatives are especially useful in that they demonstrate very low peripheral toxicity or no peripheral toxicity In some embodiments, the subject is administered an effective amount of a fatty acid COX inhibitor derivative.

The fatty acid. COX inhibitor derivatives can each be administered in amounts that are sufficient to treat or prevent a metabolic disease or prevent the development thereof in subjects.

Administration of the fatty acid. COX inhibitor derivatives can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a fatty acid COX inhibitor derivative and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate; sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the fatty acid COX inhibitor derivative is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the fatty acid COX inhibitor derivatives.

The fatty acid COX inhibitor derivatives can be also formulated as a suppository that can be prepared from fatty emulsions or suspensions; using polyalkylene glycols such as propylene glycol, as the carrier.

The fatty acid COX inhibitor derivatives can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, the contents of which are herein incorporated by reference in their entirety.

Fatty acid COX inhibitor derivatives can also be delivered by the use of monoclonal antibodies as individual carriers to which the fatty acid COX inhibitor derivatives are coupled. The fatty acid COX inhibitor derivatives can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the fatty acid COX inhibitor derivatives can be coupled to a class of biodegradable polymers useful in achieving controlled release, of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, fatty acid COX inhibitor derivatives are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 90%, from about 10% to about 90%, or from about 30% to about 90% of the fatty acid COX inhibitor derivative by weight or volume.

The dosage regimen utilizing the fatty acid COX inhibitor derivative is selected in accordance with a variety of factors including type, species, age, weight, sex and medical condition of the patient; the severity of the condition to be treated; the route of administration; the renal or hepatic function of the patient; and the particular fatty acid COX inhibitor derivative employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 20 mg to about 5,000 mg of the fatty acid COX inhibitor derivative per day. Compositions for in vivo or in vitro use can contain about 20, 50, 75, 100, 150, 250, 500, 750, 1,000, 1,250, 2,500, 3,500, or 5,000 mg of the fatty acid COX inhibitor derivative. In one embodiment, the compositions are in the form of a tablet that can be scored. Effective plasma levels of the fatty acid COX inhibitor derivative can range from about 5 ng/mL to about 5,000 ng/mL. Appropriate dosages of the fatty acid COX inhibitor derivatives can be determined as set forth in Goodman, L. S.; Gilman, A. *The Pharmacological Basis of Therapeutics,* 5th ed.; MacMillan: New York, 1975, pp. 201-226.

Fatty acid COX inhibitor derivatives can be administered in a single daily dose, or the total daily dosage can be administered in divided doses of two, three or four times daily. Furthermore, fatty acid COX inhibitor derivatives can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the fatty acid COX inhibitor derivative ranges from about 0.1% to about 15%, w/w or w/v.

Methods for Making the Fatty Acid COX Inhibitor Derivatives

Examples of synthetic pathways useful for making fatty acid COX inhibitor derivatives of Formula I are set forth in the Examples below and generalized in Schemes 1-10.

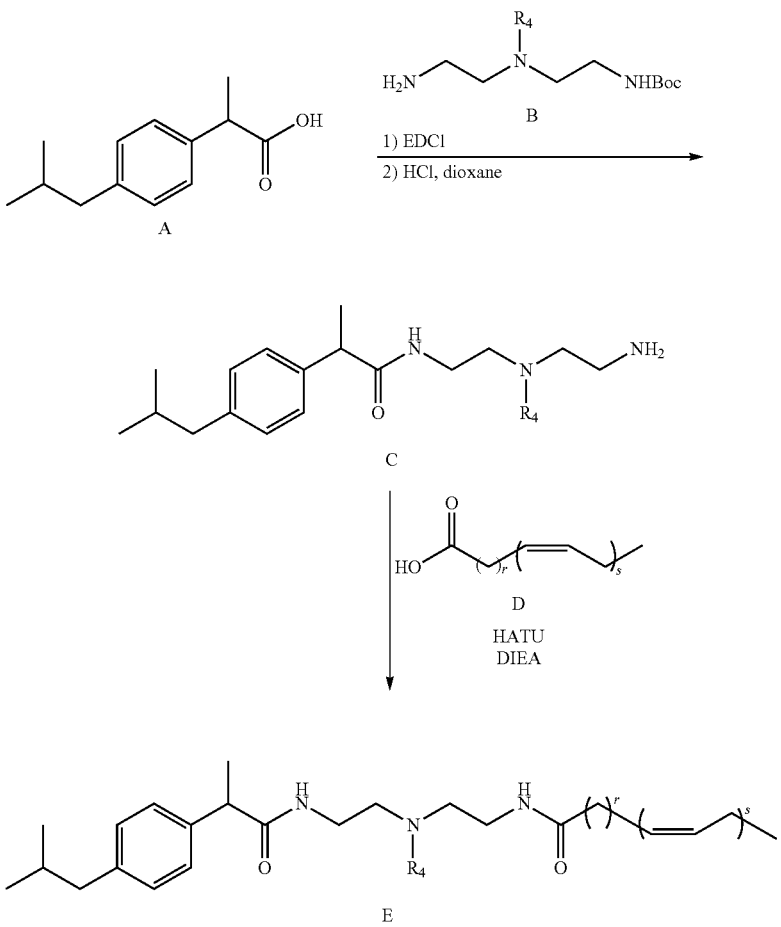

wherein $R_4$, r, and s are as defined above.

The mono-BOC protected amine of the formula B can be obtained from commercial sources or prepared according to the procedures outlined in Krapcho et al. *Synthetic Commun.* 1990, 20, 2559-2564. The commercially available compound A can be amidated with the amine B using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound C. Activation of compound C with a coupling agent such as HATU in the presence of an amine such as DIEA followed by addition of a fatty acid of formula D affords compounds of the formula E. To those familiar in the art, the fatty acid D can also be substituted with lipoic acid in this scheme and in the subsequent schemes.

Scheme 2

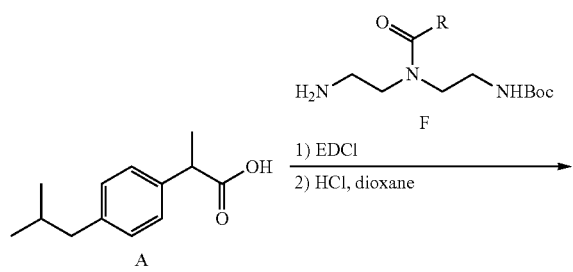

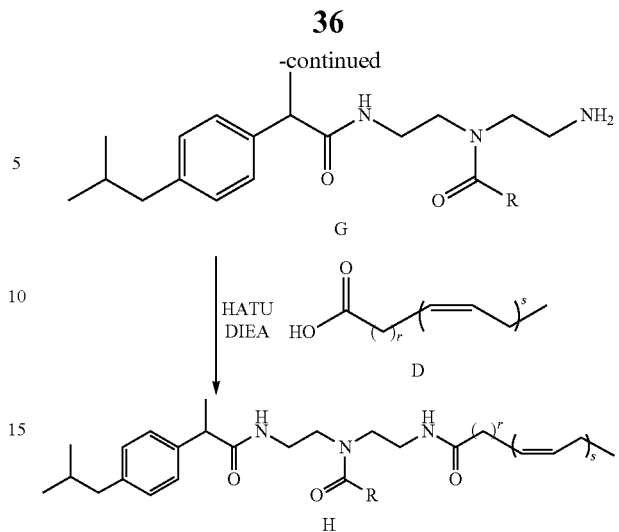

wherein R, r, and s are as defined above.

The acylated amine of the formula F can be prepared using the procedures outlined in Andruszkiewicz et al. *Synthetic Commun.* 2008, 38, 905-913. Compound A can be amidated with the amine F Using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound G. Activation of compound G with a coupling agent such as HATU in the presence of an amine such as DIEA followed by addition of a fatty acid of formula D affords compounds of the formula H.

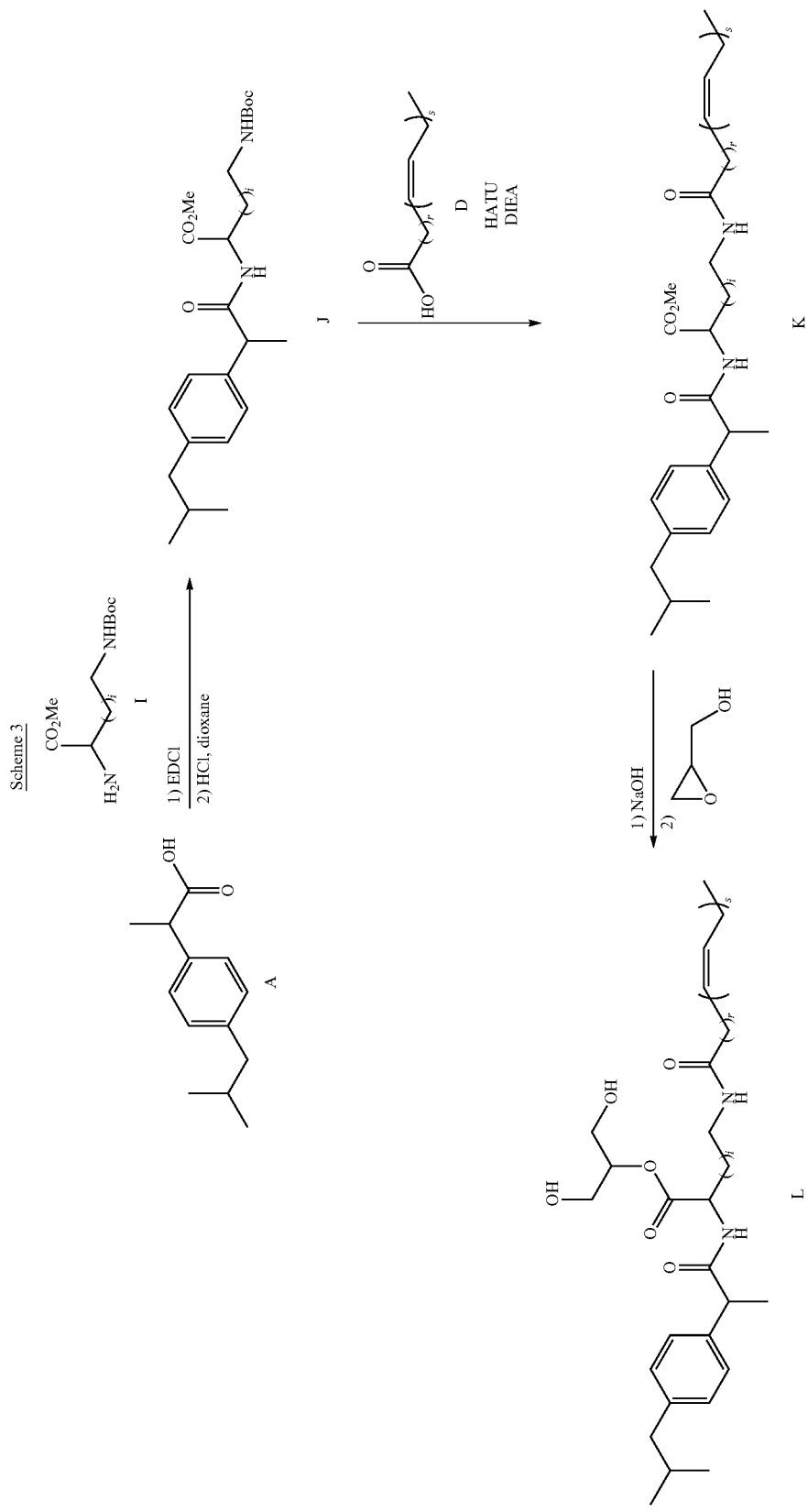

wherein r and s are as defined above.

Compound A can be amidated with the corresponding amine I (where i=0, 1, 2 or 3) using a coupling reagent such as DCC, CDI, EDC, or optionally with a tertiary amine base and/or catalyst, e.g., DMAP, followed by deprotection of the BOC group with, acids such as TFA or HCl in a solvent such as CH$_2$Cl$_2$ or dioxane to produce the coupled compound J.

Activation of compound J with a coupling agent such as HATU in the presence of an amine such as DIEA followed by addition of a fatty acid of formula D affords compounds of the formula K. Hydrolysis of the ester under basic conditions such as NaOH or LiOH produces the corresponding acid, which can be coupled with glycidol to afford compounds of the formula L.

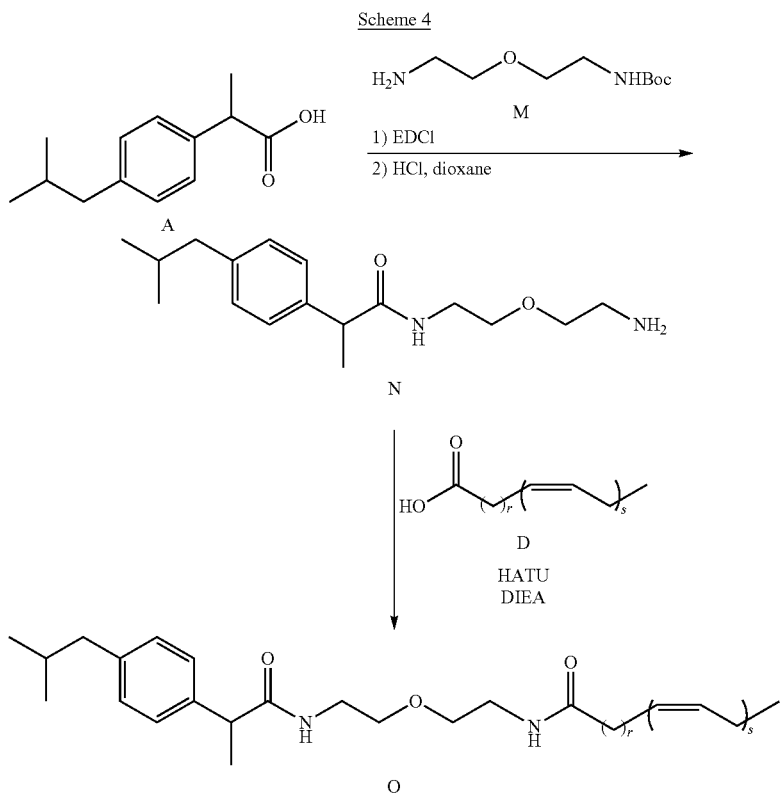

wherein r and s are as defined above.

The amine M can be prepared according to the procedures outlined in Dahan et al. *J. Org. Chem.* 2007, 72, 2289-2296. Compound A can be coupled with the amine M using a coupling reagent such as DCC, CDI, EDC, or optionally with a tertiary amine base and/or catalyst, e.g., DMAP, followed by deprotection of the BOC group with acids such as TFA or HCl in a solvent such as CH$_2$Cl$_2$ or dioxane to produce the coupled compound N. Activation of compound N with a coupling agent such as HATU in the presence of an amine such as DIEA followed by addition of a fatty acid of formula D affords compounds of the formula O.

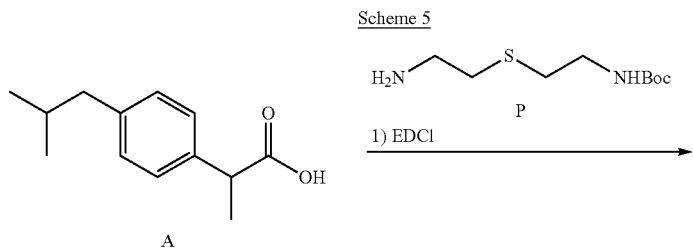

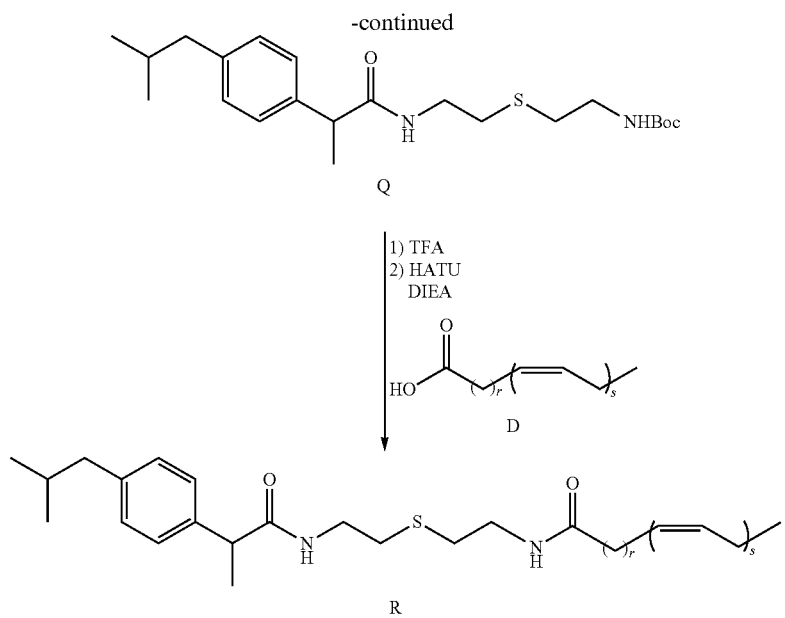

wherein r and s are as defined above.

Compound A can be amidated with the commercially available amine P using a coupling reagent such as DCC, CDI, EDC, or optionally with a tertiary amine base and/or catalyst, e.g., DMAP, to afford compound Q. The BOC group in compound Q can be removed with acids such as TFA or HCl in a solvent such as $CH_2Cl_2$ or dioxane and the resulting amine can be coupled with a fatty acid of formula D using a coupling agent such as HATU in the presence of an amine such as DIEA to afford compounds of the formula R. To those skilled in the art, the sulfur group in formula Q can be oxidized to the corresponding sulfoxide or sulfone using an oxidizing agent such as $H_2O_2$ or oxone.

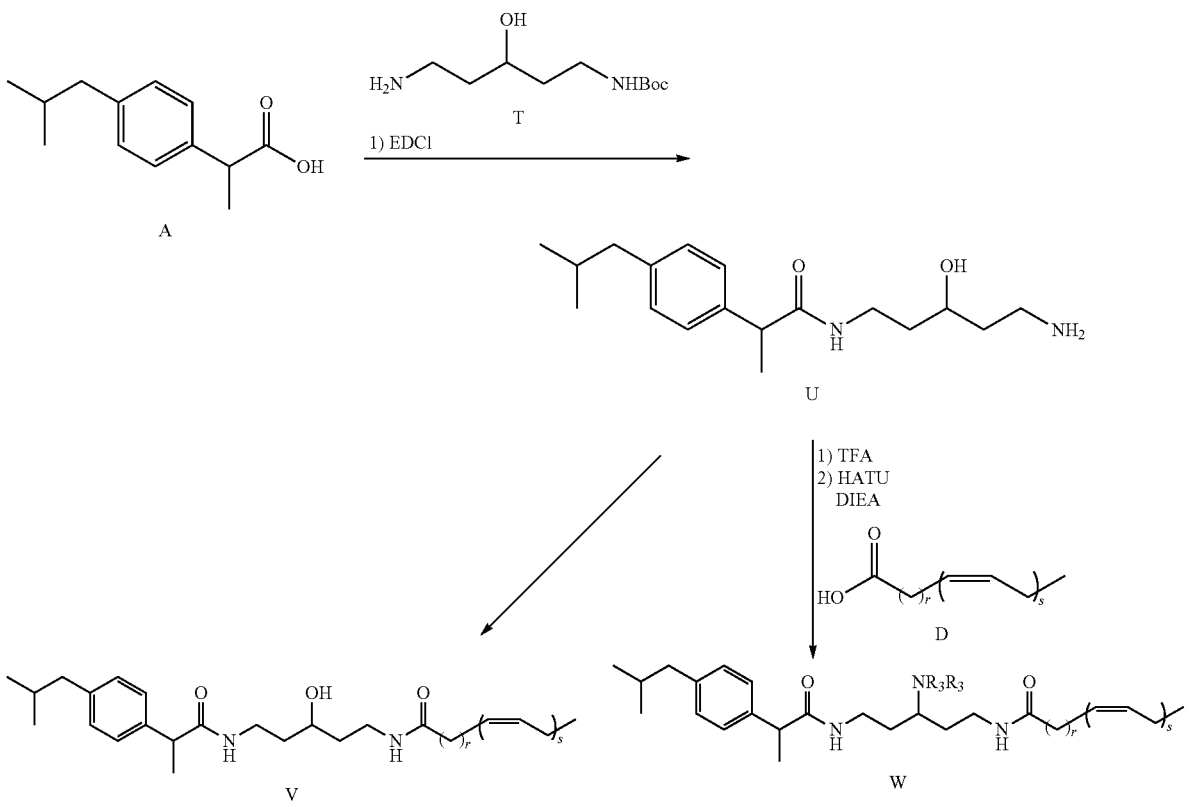

wherein $R_3$, r, and s are as defined above.

The amine T can be prepared from the commercially available diamine according to the procedures outlined in Dahan et al. *J. Org. Chem.* 2007, 72, 2289-2296. Compound A can be amidated with the amine T using a coupling reagent such as DCC, CDI, EDC, or optionally with a tertiary amine base and/or catalyst, e.g., DMAP, to afford compound U. The BOC group of compound U can be removed with acids such as TFA or HCl in a solvent such as $CH_2Cl_2$ or dioxane and the resulting amine can be coupled with a fatty acid of formula D using HATU in the presence of an amine such as DIEA to afford compounds of the formula V. To those skilled in the art, the hydroxyl group in compound U can be further acylated or converted to an amino group by standard mesylation chemistry followed by displacement with sodium azide and hydrogenation over a catalyst such as Pd/C. The amine can be further acylated or alkylated, followed by the removal of the BOC group. The resulting amine can be coupled with a fatty acid of the formula D to afford compounds of the formula W.

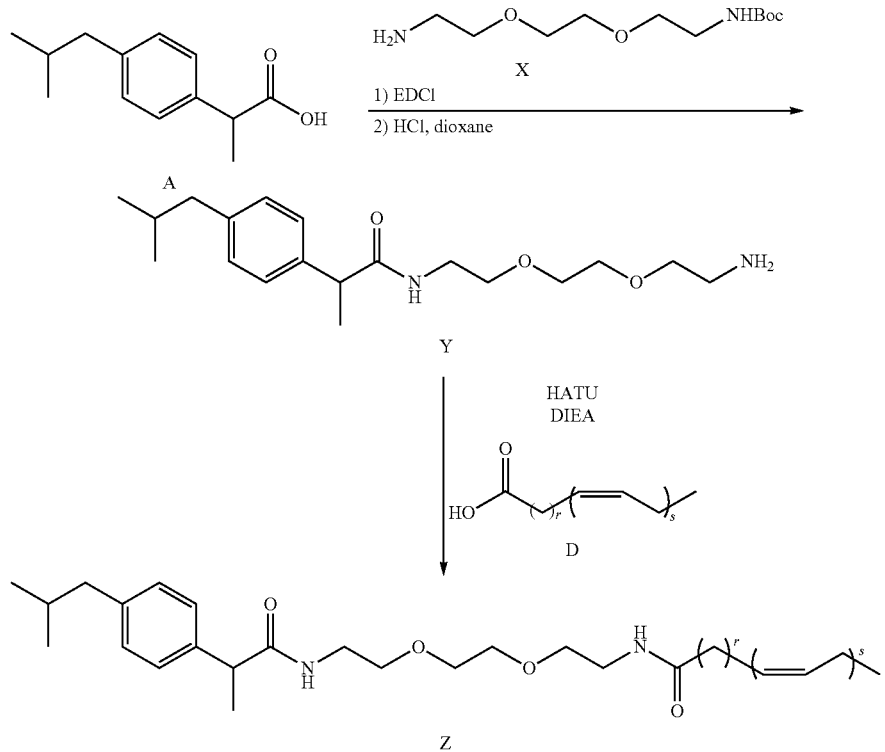

Scheme 7 wherein r and s are as defined above.

Compound A can be amidated with the commercially available amine X using a coupling reagent such as DCC, CDI, EDC, optionally with a tertiary amine base and/or catalyst, e.g., DMAP to afford compound Y. The BOC group in compound Y can be removed with acids such as TFA or HCl in a solvent such as $CH_2Cl_2$ or dioxane. The resulting amine can be coupled with a fatty acid of the formula D using a coupling agent such as HATU in the presence of an amine such as DIEA to afford compounds of the formula Z.

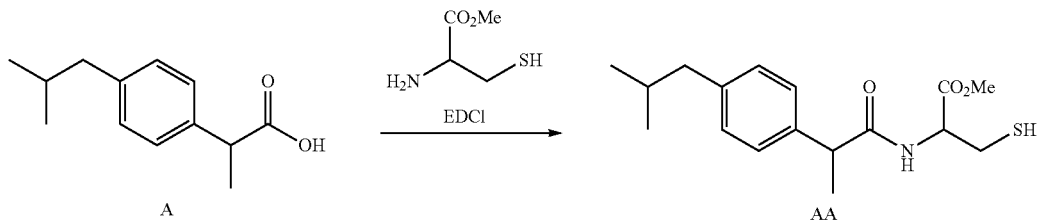

Scheme 8

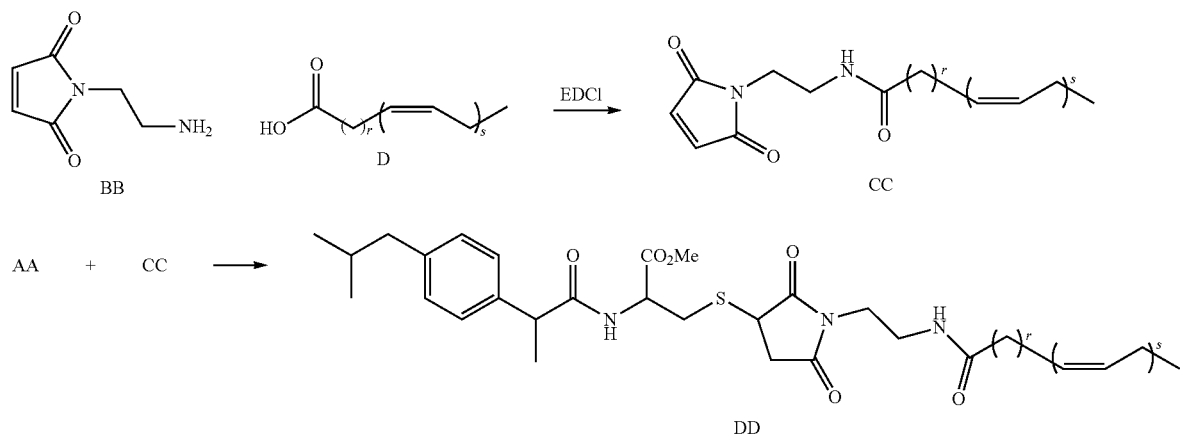

wherein r and s are as defined above.

Compound A can be amidated with the commercially available cysteine methyl ester using a coupling reagent such as DCC, CDI, EDC, or optionally with a tertiary amine base and/or catalyst, e.g., DMAP, to afford compound AA. The commercially available maleimide derivative BB can be coupled with a fatty acid of the formula D using a coupling agent such as HATU or EDCI to afford compounds of the formula CC. Compound AA can be coupled to compounds of the formula CC in a solvent such as acetonitrile to afford compounds of the formula DD.

Scheme 9

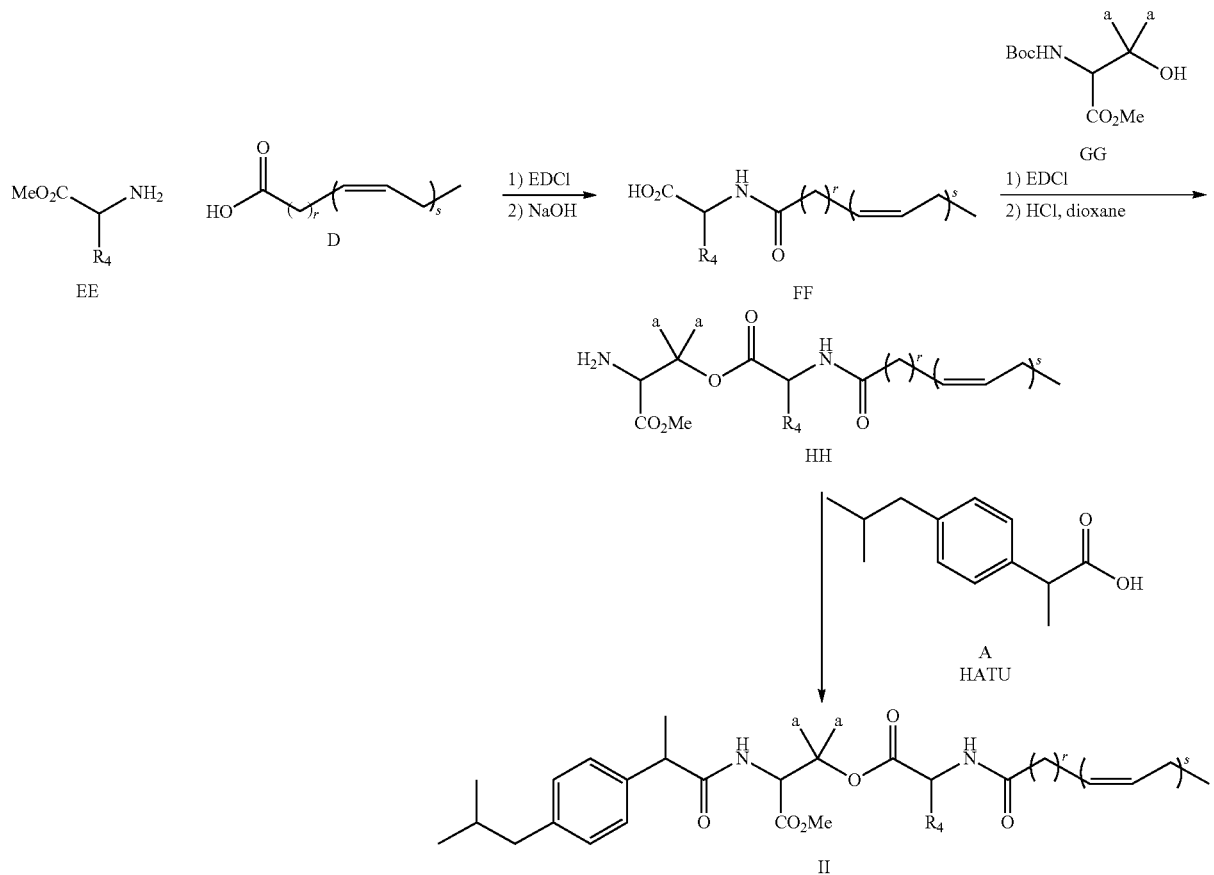

wherein $R_4$, a, r, and s are as defined above:

The commercially available amino acid esters EE can be coupled with a fatty acid of the formula D using a coupling agent such as EDCI or HATU, followed by alkaline hydrolysis of the methyl ester to afford compounds of the formula FF. Compounds of the formula FF can be coupled with the commercially available BOC-amino acid derivatives GG using a coupling agent such as EDCI or HATU. The BOC group can be removed by treatment with acids such as TFA or HCl to afford compounds of the formula HH which can then be coupled with compound A to afford compounds of the formula II.

Scheme 10

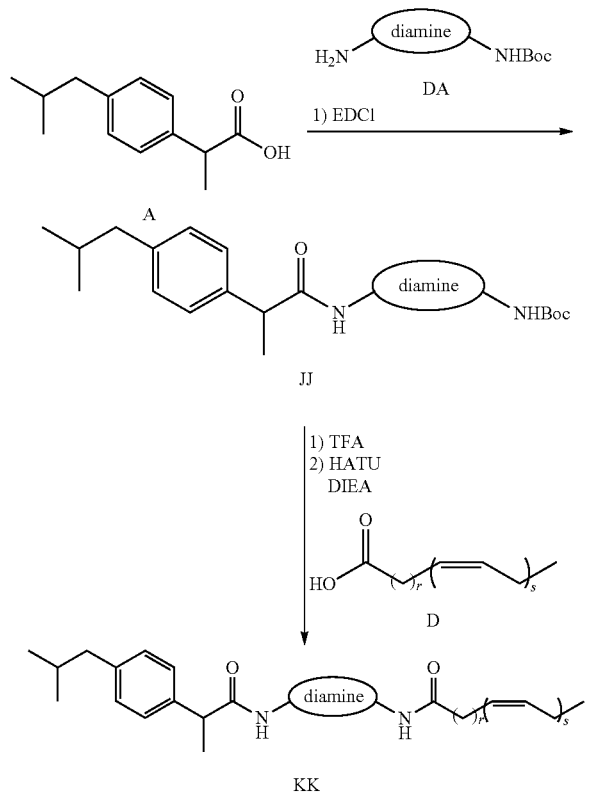

A fatty acid of formula A can be coupled with a BOC-protected diamine of the general formula DA to obtain the BOC-protected amide derivative. After treatment with HCl in dioxane, the resulting amine can be coupled with a fatty acid of the formula D in order to obtain compounds of the formula KK. A variety of BOC-protected diamines are commercially available. The following diamines can be prepared according to the procedures outlined in the corresponding references:

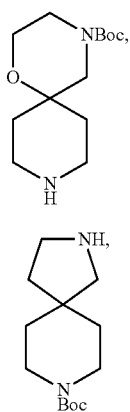

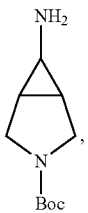

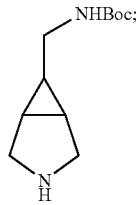

diamine DA1, Stocks et al, *Bioorganic and Medicinal Chemistry Letters* 2010, p. 7458; diamine DA2, Fritch et al, *Bioorganic and Medicinal Chemistry Letters* 2010, p. 6375; diamine DA3 and DA4, Moffat et al, *J. Med. Chem.* 2010, 53, p. 8663-8678). To those familiar in the art, detailed procedures to prepare a variety of mono-protected diamines can also be found in the following references: WO 2004092172, WO 2004092171, and WO 2004092173.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Effect of the Compounds of the Invention on HMOX-1 and IL-1β

RAW264.7 macrophages are seeded at a density of 100,000 cells/well in a 96-well plate in DMEM supplemented with 10% FBS and Penn/strep. 16 hours later, medium is aspirated and, replaced with 90 μL/well of serum-free DMEM. The compounds of the invention are brought up in 100% EtOH to a concentration of 100 mM and then diluted 1:100 in 100% FBS for a stock solution consisting of 1 mM compound and 1% EtOH. These stock solutions are then diluted 1:10 in FBS supplemented with 1% EtOH to generate a 100 μM of the fatty acid COX inhibitor. 10 μL is then added to the RAW246.7 cells to generate final concentrations of 10 μM of the fatty acid COX inhibitor along with vehicle only control. The compounds are allowed to pre-incubate for 2 hours before stimulation of 100 ng/ml LPS (10 μL of 1 μg/ml LPS is added to each well). Following 3 hours of LPS stimulation, cells are washed once in 1×PBS, aspirated dry, and flash frozen in liquid nitrogen. RNA is then isolated and converted to cDNA using the Cells to cDNA kit (Ambion) according to the manufacturer's protocol. HMOX-1 and IL-1β transcript levels are then measured using Taqman primer/probe assay sets (Applied Biosystems), normalized to GAPDH using the deltaCt method, and the data expressed relative to vehicle only control.

Example 2

Effects of the Compounds of the Invention on COX Activity

Cyclooxygenase (COX) is a bifunctional enzyme exhibiting both cyclooxygenase and peroxidase activities. The cyclooxygenase activity first converts arachidonic acid to a hydroperoxy endoperoxide (PGG2) and then the peroxidase activity reduces the endoperoxide to an alcohol (PGH2). PGH2 is the precursor to all prostaglandins (as well as thromboxanes and prostacyclins) by tissue-specific isomerases to create both pro- and anti-inflammatory prostaglandins. The peroxidase activity of both COX-1 and COX-2 can be measured in RAW264.7 macrophages. RAW264.7 macrophages, in turn, can be seeded and prepared according to the protocols outlined in example 1 and treated with the compounds of the invention or left untreated (vehicle control). The compounds of the invention are brought up in 100% EtOH to a concentration of 100 mM and then diluted 1:100 in 100% FBS for a stock solution consisting of 1 mM compound and 1% EtOH using the same protocols outlined in example 1 above. The peroxidase activity of both COX-1 and Cox-2 in treated cells can then be measured by the appearance of oxidized N,N,N',N'-tetramethyl-p-phenylenediamine (TMPD) at 590 nM. The relative effects of the compounds on each COX isoform will be determined by incorporating COX-1 specific (SC-590) and COX-2 specific (DuP-697) inhibitors. Cox activity will be measured in vitro using a commercially available Cox activity assay kit (Cayman Chemicals, cat #760151) according to the manufacturer's instructions.

Example 3

Effects of the Compounds of the Invention in an in vivo Prostaglandin E2 (PGE2) Metabolite Assay Prostaglandin E2 (PGE2) is rapidly converted in vivo to its 13,14-dihydro-15-keto metabolite, with more than 90% of circulating PGE2 cleared by a single passage through the lungs. Unfortunately, this metabolite is not chemically stable and undergoes a variable amount of degradation to Prostaglandin A products. For this reason, blood, urine, or other samples from whole animals or humans often contain very little intact PGE2, and measurement of the metabolites is necessary to provide a reliable estimate of actual PGE2 production. To measure effects of compounds of the invention in animal models, the commercially available Cayman Chemical's PGE Metabolite assay (cat #514531) will be employed. This kit essentially converts 13,14-dihydro-15-keto PGA2 and 13,14-dihydro-15-keto PGE2 to a single, stable derivative that could be easily quantified by ELISA. Briefly, the assay is based on the competition between Prostaglandin E Metabolite (PGEM) and a PGEM-acetylcohinesterase (AChE) conjugate (PGEM Tracer) for a limited number of PGEM-specific antibody binding, sites, and thus the signal is inversely proportional to the amount of PGEM found in the urine or plasma. C57BL/6 female mice that are 8-12 weeks old with body weight in the range of 20-30 g can be used for the study. Mice (in groups of 10) are treated acutely with either the vehicle (control group) or the compounds of the invention by either ip or oral gavage. All compounds are formulated in the appropriate vehicles (Examples of vehicles that can be used include combinations of solvents such as polyethylene glycol and propyleneglycol, lipids such as glycerol monooleate and soybean oil, and surfactants such as polysorbate 80 and cremophor EL). Ninety minutes after compound dosing, animals are treated with 0.2 mg/kg LPS (lipopolysaccharide) by intraperitoneal (IP) injection. Ninety minutes after LPS challenge, mice are anesthetized and bled by cardiac puncture into serum separator tubes (with sodium heparin). Bleeds are allowed to clot at room temperature for 2 hours, and tubes are then spun for 20 minutes at 2,000×g. Serum is harvested from tubes (100-150 µL per animal) and frozen at −70° C. PGE2 levels are then measured indirectly using, the commercially available Cayman Chemical's PGE Metabolite assay (cat #514531) according to the manufacturer's instructions.

Alternatively, the effect of the compounds of the invention on PGE2 can also be carried out in RAW264.7 macrophages that have been stimulated with LPS using the same commercially available PGE2 Metabolite assay. RAW264.7 macrophages are prepared and treated with the compounds of the invention and then exposed to LPS stimulation according to the protocols outlined above in Example 1.

Compounds

The following non-limiting compound examples serve to illustrate further embodiments of the fatty acid COX inhibitor derivatives. It is to be understood that any embodiments listed in the Examples section are embodiments of the fatty acid COX inhibitor derivatives and, as such, are suitable for use in the methods and compositions described above.

Example 4

Preparation of (4Z,7Z,10Z,13Z,16Z,19Z)—N-(2-(2-(1-(4-chlorobenzoyl)-5-methoxy-2-methyl-1H-indol-3-yl)acetamido)ethyl)docosa-4,7,10,13,16,19-hexaenamide (I-11)

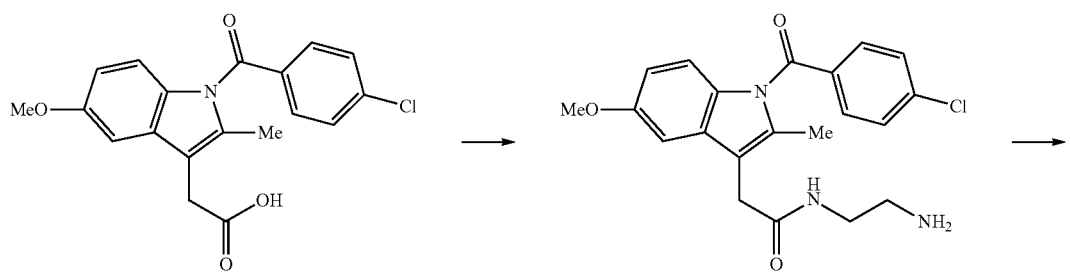

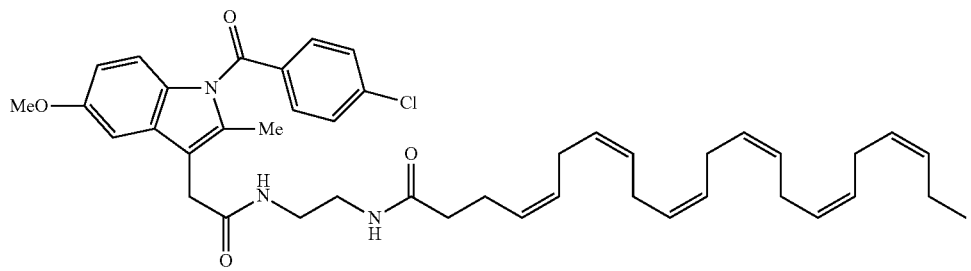

Indomethacin (500 mg, 1.40 mmol) was taken up in 10 mL of $CH_2Cl_2$ along with tert-butyl 2-aminoethylcarbamate (223 mg, 1.40 mmol) and EDC (295 mg, 1.54 mmol). The resulting reaction mixture was stirred at room temperature for 18 and diluted with $CH_2Cl_2$ (10 mL). The organic layer was washed with brine, dried ($Na_2SO_4$) and concentrated under reduced pressure. Purification by chromatography (95% $CH_2Cl_2$, 5% MeOH) afforded 550 mg of tert-butyl 2-(2-(1-(4-chlorobenzoyl)-5-methoxy-2-methyl-1H-indol-3-yl)acetamido)ethylcarbamate (79% yield).

tert-Butyl 2-(2-(1-(4-chlorobenzoyl)-5-methoxy-2-methyl-1H-indol-3-yl)acetamido)ethylcarbamate (275 mg, 0.55 mmol) was taken up in 6 mL of 4 M HCl in dioxane and allowed to stir at room temperature for 1 h. It was then (lilted with EtOAc (10 mL) and concentrated under reduced pressure to afford the HCl salt of N-(2-aminoethyl)-2-(1-(4-chlorobenzoyl)-5-methoxy-2-methyl-1H-indol-3-yl)acetamide. This material was taken up in 6 mL of $CH_3CN$ along with DHA (180 mg, 0.55 mmol), HATU (230 mg, 0.605 mmol) and DIEA (290 µL, 1.7 mmol). The resulting reaction mixture was stirred at room temperature for 2 h and diluted with EtOAc (30 mL). The organic layer was washed with brine, dried ($Na_2SO_4$) and concentrated under reduced pressure. Purification by silica gel chromatography (95% $CH_2Cl_2$, 5% MeOH) afforded 200 mg of (4Z,7Z,10Z,13Z,16Z,19Z)—N-(2-(2-(1-(4-chlorobenzoyl)-5-methoxy-2-methyl-1H-indol-3-yl)acetamido)ethyl)docosa-4,7,10,13,16,19-hexaenamide (51% yield). MS (EI) calcd for $C_{45}H_{52}ClN_3O_4$: 709.36; found 710 (M+1).

Example 5

Preparation of (5Z,8Z,11Z,14Z,17Z)—N-(2-(2-(1-(4-chlorobenzoyl)-5-methoxy-2-methyl-1H-indol-3-yl)acetamido)ethyl)icosa-5,8,11,14,17-pentaenamide (I-12)

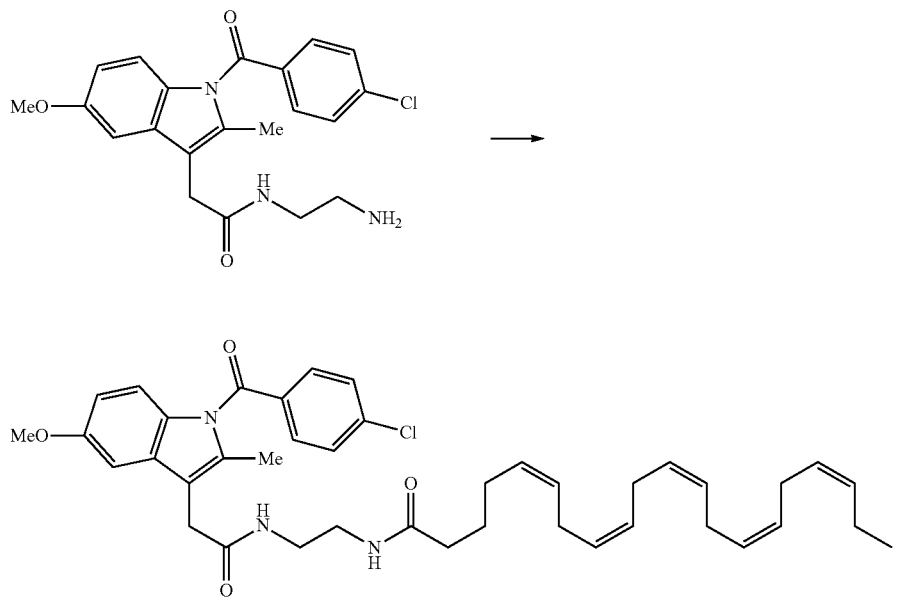

The same experimental procedure detailed above for the preparation of (4Z,7Z,10Z,13Z,16Z,19Z)—N-(2-(2-(2-(1-(4-chlorobenzoyl)-5-methoxy-2-methyl-1H-indol-3-yl)acetamido)ethoxy)ethyl)docosa-4,7,10,13,16,19-hexaenamide was used, substituting. EPA for DHA. MS (EI) calcd for $C_{41}H_{50}ClN_3O_4$: 683.35; found 684 (M+1).

Example 6

Preparation of (4Z,7Z,10Z,13Z,16Z,19Z)—N-(2-(2-(2-(1-(4-chlorobenzoyl)-5-methoxy-2-methyl-1H-indol-3-yl)acetamido)ethoxy)ethyl)docosa-4,7,10,13,16,19-hexaenamide (I-13)

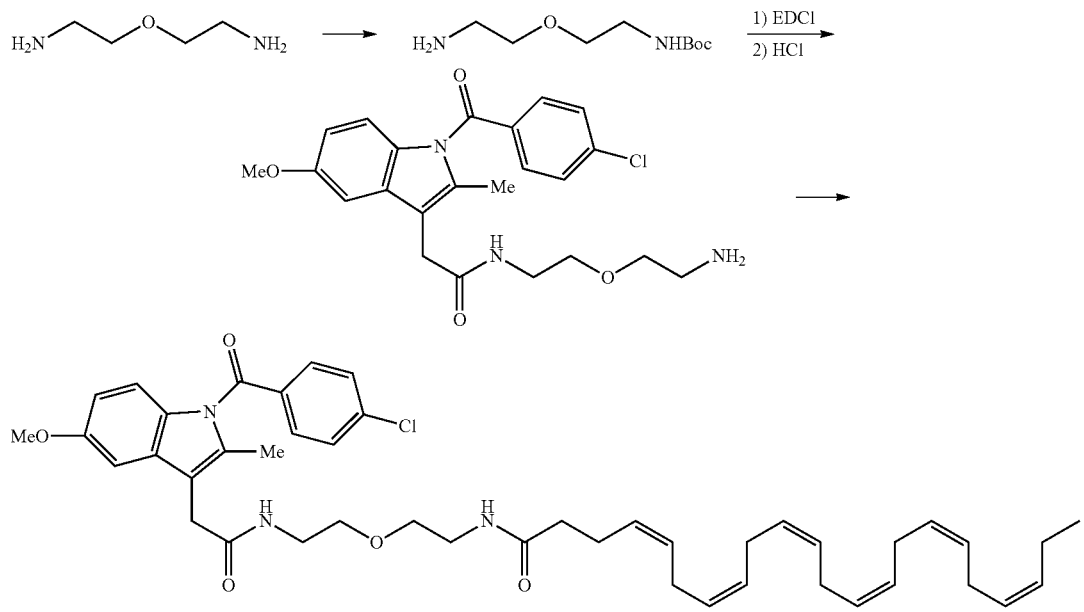

In a typical run, sodium hydroxide (400 mg, 10 mmol) is dissolved in MeOH (70 L) and 2-(2-aminoethoxy)ethanamine dihydrochloride (1.0 g, 5.65 mmol) is added. The resulting reaction mixture is stirred at room temperature for 30 min. A solution containing $Boc_2O$ (740 mg, 3.40 mmol) in THF (15 mL) is then added dropwise, at room temperature, over a period of 15 min. The resulting reaction mixture is stirred at room temperature for 18 h and then concentrated under reduced pressure. The resulting residue is taken up in $CH_2Cl_2$ (200 mL) and stirred vigorously at room temperature for 4 h. The mixture is filtered and the filtrate is concentrated under reduced pressure to afford 850 mg of tert-butyl 2-(2-aminoethoxy)ethylcarbamate (74% yield).

tert-Butyl 2-(2-aminoethoxy)ethylcarbamate (150 mg, 0.735 mmol) was then taken up in $CH_3CN$ (10 mL) along with indomethacin (263 mg, 0.735 mmol) and EDCI (155 mg, 0.81 mmol). The resulting reaction mixture was stirred at room temperature for 18 h. It was then diluted with EtOAc (20 mL), washed with saturated aqueous $NaHCO_3$, brine, dried over $Na_2SO_4$, filtered and concentrated under reduced pressure. The resulting residue was purified by silica gel chromatography (9:1 $CH_2Cl_2$/MeOH) to afford 310 mg of tert-butyl 2-(2-(2-(1-(4-chlorobenzoyl)-5-methoxy-2-methyl-1H-indol-3-yl)acetamido)ethoxy)ethylcarbamate (78%).

tert-Butyl 2-(2-(2-(1-(4-chlorobenzoyl)-5-methoxy-2-methyl-1H-indol-3-yl)acetamido)ethoxy)ethylcarbamate was taken up in 10 mL of 4 M HCl in dioxane and allowed to stand at room temperature for 2 h. The resulting reaction mixture was concentrated under reduced pressure to afford the HCl salt of N-(2-(2-aminoethoxy)ethyl)-2-(1-(4-chlorobenzoyl)-5-methoxy-2-methyl-1H-indol-3-yl)acetamide. This material was taken up in $CH_3CN$ (10 mL) along with (4Z,7Z,10Z, 13Z,16Z,19Z)-docosa-4,7,10,13,16,19-hexaenoic acid (187 mg, 0.57 mmol), HATU (238 mg, 0.63 mmol) and DIEA (300 μL, 1.71 mmol). The resulting reaction mixture was stirred at room temperature for 2 h, diluted with EtOAc and washed successively with saturated aqueous $NaHCO_3$ and brine. The organic layer was dried over $Na_2SO_4$, filtered and concentrated under reduced pressure. Purification by silica gel chromatography (5% MeOH—$CH_2Cl_2$) afforded (4Z,7Z,10Z, 13Z,16Z,19Z)—N-(2-(2-(2-(1-(4-chlorobenzoyl)-5-methoxy-2-methyl-1H-indol-3-yl)acetamido)ethoxy)ethyl) docosa-4,7,10,13,16,19-hexaenamide. MS (EI) calcd for $C_{45}H_{56}ClN_3O_5$: 753.39; found 754 (M+1).

Example 7

Preparation of (4Z,7Z,10Z,13Z,16Z,19Z)—N-(2-((2-(2-(1-(4-chlorobenzoyl)-5-methoxy-2-methyl-1H-indol-3-yl)acetamido)ethyl)(methyl)amino)ethyl)docosa-4,7,10,13,16,19-hexaenamide (I-14)

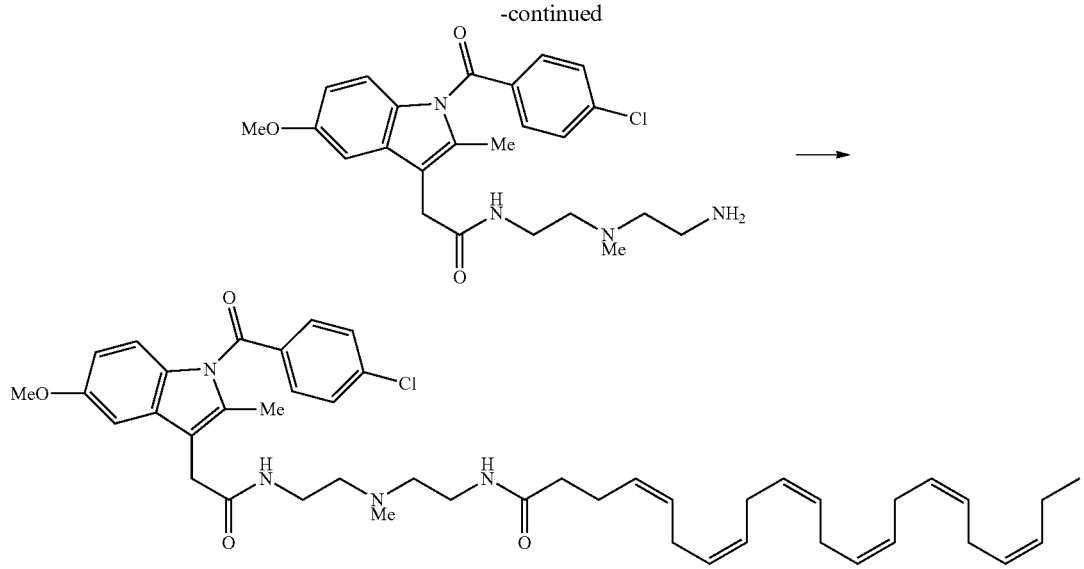

N1-(2-Aminoethyl)-N1-methylethane-1,2-diamine (5.0 g, 42.7 mmol) was dissolved in 100 mL of $CH_2Cl_2$ and cooled to 0° C. A solution of di-tert-butylcarbonate (0.93 g, 4.27 mmol) in $CH_2Cl_2$ (10 mL) was then added dropwise at 0° C. over a period of 15 mm. The resulting reaction mixture was stirred at 0° C. for 30 min and then warmed to room temperature. After stirring at room temperature for 2 h, the reaction mixture was diluted with $CH_2Cl_2$ (100 mL). The organic layer was washed with brine (3×25 mL), dried ($Na_2SO_4$) and concentrated under reduced pressure to afford 1.1 g of tert-butyl 2-((2-aminoethyl)(methyl)amino)ethylcarbamate.

tert-butyl 2-((2-aminoethyl)(methyl)amino)ethylcarbamate (150 mg, 0.69 mmol) was taken up in 10 mL of $CH_3CN$ along with indomethacin (247 mg, 0.69 mmol) and EDC (146 mg, 0.76 mmol). The resulting reaction mixture was stirred at room temperature for 2 h and then diluted with EtOAc (40 mL). The organic layer was washed with brine, dried ($Na_2SO_4$) and concentrated under reduced pressure. Purification by chromatography (95% $CH_2Cl_2$, 5% MeOH) afforded 360. Mg of the Boc-protected intermediate (93% yield). This material was taken up in 10 mL of 4 M HCl in dioxane and allowed to stir at room temperature for 10 min. The reaction mixture was concentrated under reduced pressure to afford the HCl salt of N-(2-((2-aminoethyl)(methyl)amino)ethyl)-2-(1-(4-chlorobenzoyl)-5-methoxy-2-methyl-1H-indol-3-yl)acetamide.

This HCl salt of N-(2-((2-aminoethyl)(methyl)amino)ethyl)-2-(1-(4-chlorobenzoyl)-5-methoxy-2-methyl-1H-indol-3-yl)acetamide (0.38 mmol) was taken up in 5 mL of $CH_3CN$ along with DHA (210 mg, 0.64 mmol), HATU (267 mg, 0.67 mmol) and DMA (334 μL, 2.01 mmol). The resulting reaction mixture was stirred at room temperature for 2 h and diluted with EtOAc (25 mL). The organic layer was washed with brine, dried ($Na_2SO_4$) and concentrated under reduced pressure. Purification by chromatography (95% $CH_2Cl_2$, 5% MeOH) afforded 320 mg of (4Z,7Z,10Z,13Z,16Z,19Z)—N-(2-((2-(2-(1-(4-chlorobenzoyl)-5-methoxy-2-methyl-1H-indol-3-yl)acetamido)ethyl)(methyl)amino)ethyl)docosa-4,7,10,13,16,19-hexaenamide (65% yield). MS (EI) calcd for $C_{46}H_{59}ClN_4O_4$: 766.42; found 767 (M+1).

Example 8

Preparation of (4Z,7Z,10Z,13Z,16Z,19Z)—N-(2-(2-(2-(2-(1-(4-chlorobenzoyl)-5-methoxy-2-methyl-1H-indol-3-yl)acetamido)ethyl)disulfanyl)ethyl)docosa-4,7,10,13,16,19-hexaenamide (I-15)

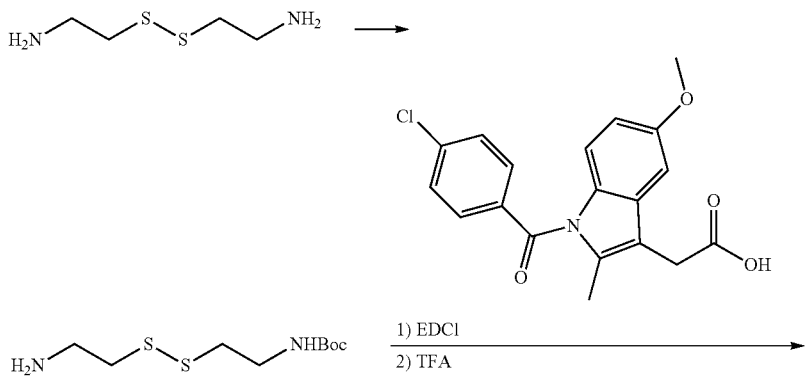

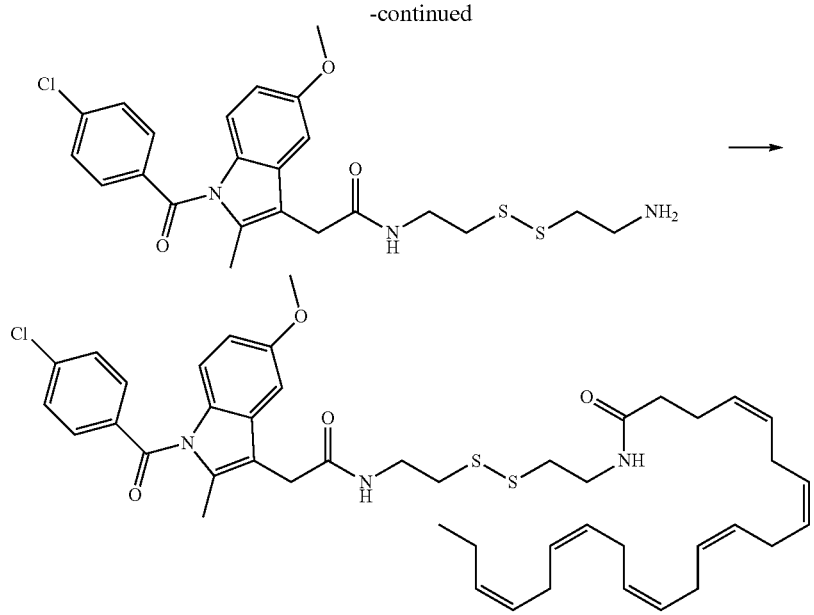

Cystamine dihydrochloride (1.0 g, 4.44 mmol) was dissolved in MeOH (50 mL). Triethylamine (1.85 mL, 3 eq) was added at room temperature, followed by dropwise addition of Boc$_2$O (0.97 g, 4.44 mmol) as a solution in MeOH (5 mL). The resulting reaction mixture was stirred at room temperature for 3 h, concentrated under reduced pressure and the resulting residue was taken up in 1M aqueous NaH$_2$PO$_4$ (20 mL). The aqueous layer was washed with a 1:1 solution of pentane/EtOAc (10 mL), basified to pH 9 with 1M aqueous NaOH, and extracted with EtOAc. The combined organic layers were washed with brine, dried over Na$_2$SO$_4$, filtered and concentrated under reduced pressure to afford tert-butyl 2-(2-(2-aminoethyl)disulfanyl)ethylcarbamate (500 mg, 44% yield).

tert-Butyl 2-(2-(2-aminoethyl)disulfanyl)ethylcarbamate (150 mg, 0.595 mmol) was taken up in CH$_2$C$_2$ (10 mL) along with indomethacin (213 mg, 0.595 mmol) and EDCI (125 mg, 0.65 mmol). The resulting reaction mixture was stirred at room temperature for 18 h and diluted with CH$_2$Cl$_2$. The organic layer was washed with saturated aqueous NaHCO$_3$, brine, dried over Na$_2$SO$_4$, filtered and concentrated under reduced pressure. The resulting residue was purified by chromatography (CH$_2$Cl$_2$) to afford 312 mg of tert-butyl 2-(2-(2-(1-(4-chlorobenzoyl)-5-methoxy-2-methyl-1H-indol-3-yl)acetamido)ethyl)disulfanyl)ethylcarbamate (89% yield).

tert-Butyl 2-(2-(2-(1-(4-chlorobenzoyl)-5-methoxy-2-methyl-1H-indol-3-yl)acetamido)ethyl)disulfanyl)ethylcarbamate (312 mg, 0.528 mmol) was taken up in 6 mL of 4 M HCl in dioxane and allowed to stir at room temperature for 2 h. The resulting reaction mixture was concentrated under reduced pressure to afford the HCl salt of N-(2-(2-(2-aminoethyl)disulfanyl)ethyl)-2-(1-(4-chlorobenzo yl)-5-methoxy-2-methyl-1H-indol-3-yl)acetamide. This material was taken up in CH$_3$CN (5 mL) along with (4Z,7Z,10Z,13Z,16Z,19Z)-docosa-4,7,10,13,16,19-hexaenoic acid (173 mg, 0.528 mmol), HATU (220 mg, 0.58 mmol) and DIEA (275 µL, 1.6 mmol). The resulting reaction mixture was stirred at room temperature for 2 h, diluted with EtOAc and washed successively with saturated aqueous NaHCO$_3$ and brine. The organic layer was dried over Na$_2$SO$_4$, filtered and concentrated under reduced pressure. Purification by silica gel chromatography (5% MeOH—CH$_2$Cl$_2$) afforded 220 mg of (4Z,7Z,10Z,13Z,16Z,19Z)—N-(2-(2-(2-(2-(1-(4-chlorobenzoyl)-5-methoxy-2-methyl-1H-indol-3-yl)acetamido)ethyl)disulfanyl)ethyl)docosa-4,7,10,13,16,19-hexaenamide (52% yield). MS (EI) calcd for C$_{45}$H$_{56}$ClN$_3$O$_4$S$_2$: 801.34; found 802 (M+1).

Example 9

Preparation of (S,4Z,7Z,10Z,13Z,16Z,19Z)—N-(2-(2-(6-methoxynaphthalen-2-yl)propanamido)ethyl) docosa-4,7,10,13,16,19-hexaenamide (I-7)

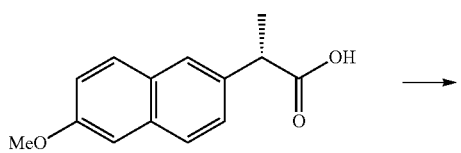

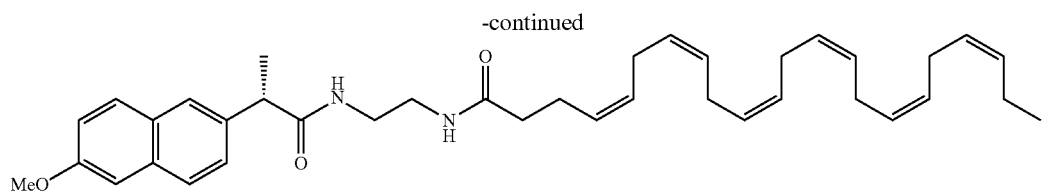

The same experimental procedure detailed above for the preparation of (4Z,7Z,10Z,13 Z,16Z,19Z)—N-(2-(2-(2-(1-(4-chlorobenzoyl)-5-methoxy-2-methyl-1H-indol-3-yl)acetamido)ethoxy)ethyl)docosa-4,7,10,13,16,19-hexaenamide was used, substituting naproxen for indomethacin. MS (EI) calcd for $C_{38}H_{50}N_2O_3$: 582.38; found 583 (M+1).

Example 10

Preparation of (4Z,7Z,10Z,13Z,16Z,19Z)—N-(2-(2-(4-isobutylphenyl)propanamido)ethyl)docosa-4,7,10,13,16,19-hexaenamide (I-1)

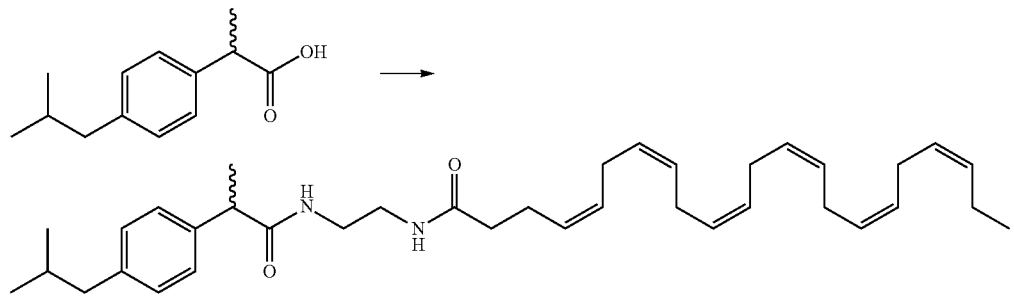

The same experimental procedure detailed above for the preparation of (4Z,7Z,10Z,13Z,16Z,19Z)—N-(2-(2-(2-(1-(4-chlorobenzoyl)-5-methoxy-2-methyl-1H-indol-3-yl)acetamido)ethoxy)ethyl)docosa-4,7,10,13,16,19-hexaenamide was used, substituting ibuprofen for indomethacin. MS (EI) calcd for $C_{37}H_{54}N_2O_7$: 558.42; found 559 (M+1).

Equivalents

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula I:

Formula I

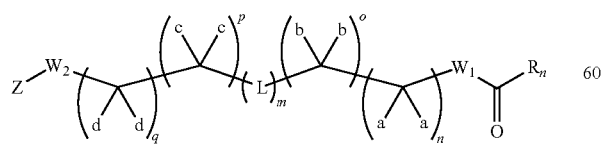

or a pharmaceutically acceptable salt, enantiomer, or stereoisomer thereof;

wherein
$R_n$ is

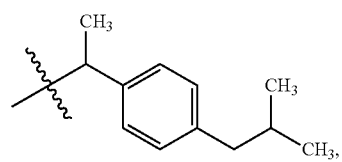

-continued

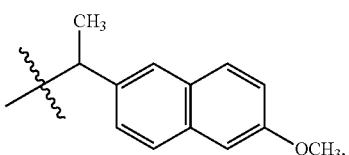

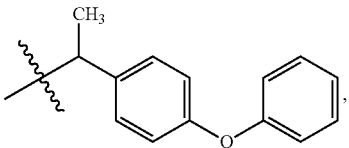

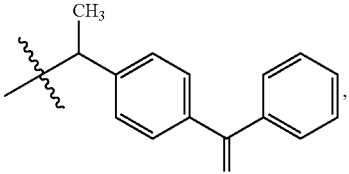

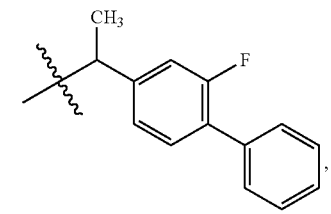

-continued

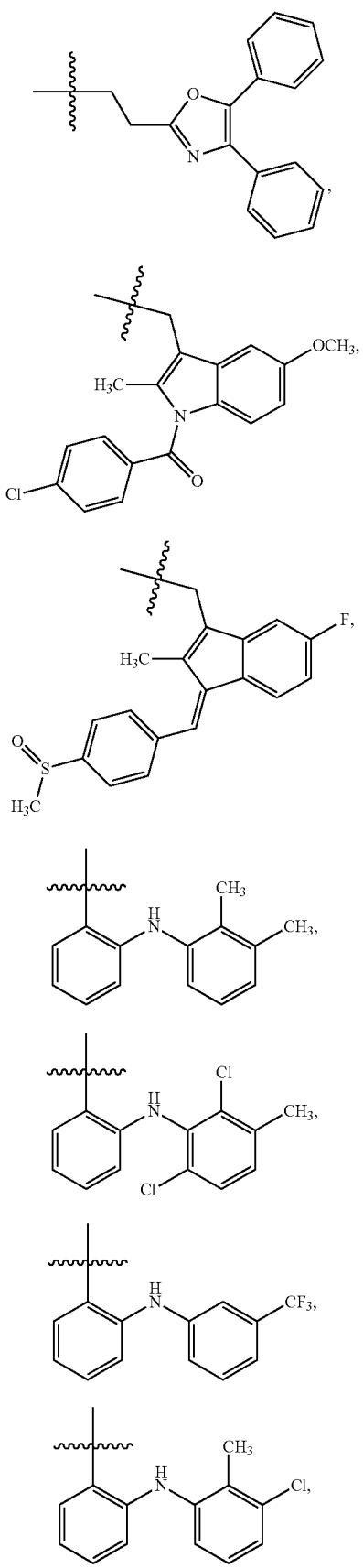

-continued

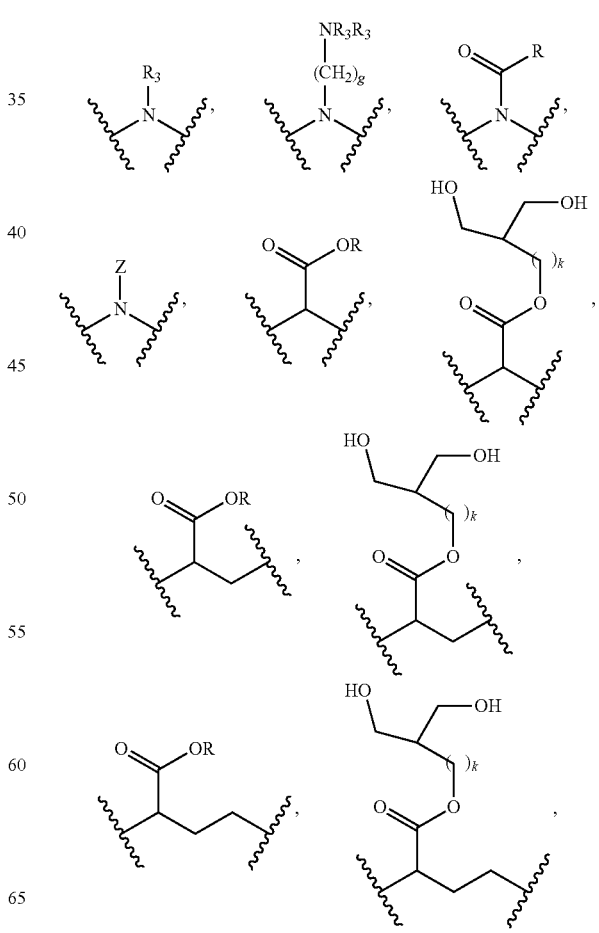

$W_1$ and $W_2$ are each independently S, NH, or NR;

each a, b, c and d is independently —H, -D, —CH$_3$, —OCH$_3$, —OCH$_2$CH$_3$, —C(O)OR, or —O—Z, or benzyl, or two of a, b, c, and d can be taken together, along with the single carbon to which they are bound, to form a cycloalkyl or heterocycle;

each n, o, p, and q is independently 0, 1 or 2;

each L is independently null, —O—, —S—, —S(O)—, —S(O)$_2$—, —S—S—, —(C$_1$-C$_6$alkyl)-, —(C$_3$-C$_6$cycloalkyl)-, a heterocycle, a heteroaryl,

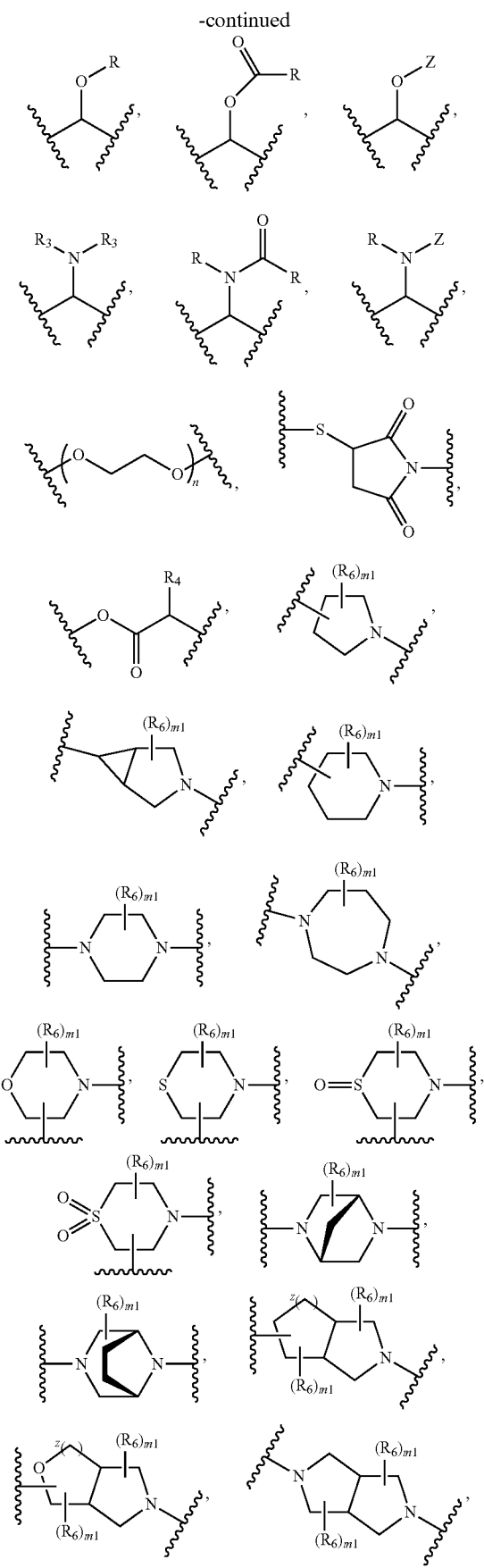
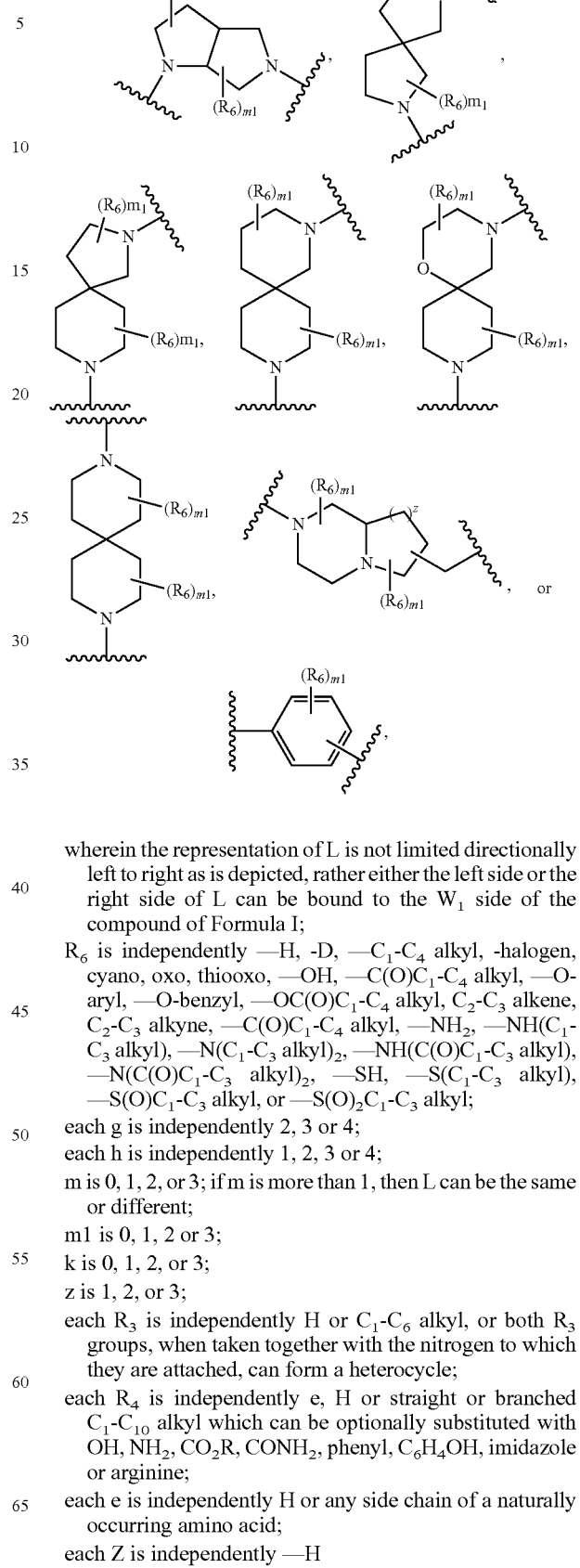

wherein the representation of L is not limited directionally left to right as is depicted, rather either the left side or the right side of L can be bound to the $W_1$ side of the compound of Formula I;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, $C_2$-$C_3$ alkene, $C_2$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2$$C_1$-$C_3$ alkyl;

each g is independently 2, 3 or 4;

each h is independently 1, 2, 3 or 4;

m is 0, 1, 2, or 3; if m is more than 1, then L can be the same or different;

m1 is 0, 1, 2 or 3;

k is 0, 1, 2, or 3;

z is 1, 2, or 3;

each $R_3$ is independently H or $C_1$-$C_6$ alkyl, or both $R_3$ groups, when taken together with the nitrogen to which they are attached, can form a heterocycle;

each $R_4$ is independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any side chain of a naturally occurring amino acid;

each Z is independently —H

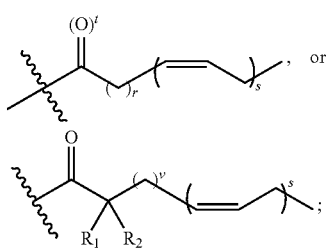, or

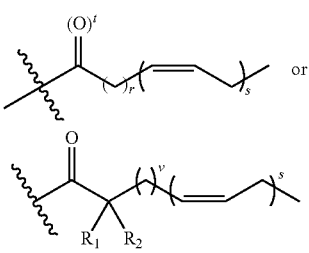;

with the proviso that there is at least one

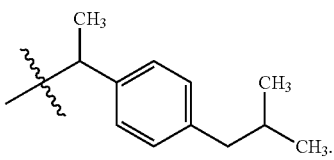 [SMILES: *C(C)c1ccc(CC(C)C)cc1] or

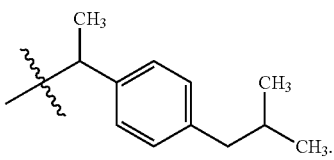 [SMILES: *C(C)c1ccc(CC(C)C)cc1]

in the compound;
each r is independently 2, 3, or 7;
each s is independently 3, 5, or 6;
each t is independently 0 or 1;
each v is independently 1, 2, or 6;
$R_1$ and $R_2$ are each independently hydrogen, deuterium, —$C_1$-$C_4$ alkyl, -halogen, —OH, —C(O)$C_1$-$C_4$ alkyl, —O-aryl, —O-benzyl, —OC(O)$C_1$—$C_4$ alkyl, $C_2$-$C_3$ alkene, $C_2$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl; and
each R is independently —H, —$C_1$-$C_3$ alkyl, or straight or branched $C_1$-$C_4$ alkyl optionally substituted with OH, or halogen.

2. The compound of claim 1, wherein $R_n$ is

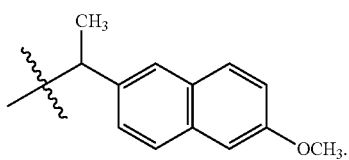 [SMILES: *C(C)c1ccc2cc(OC)ccc2c1]

3. The compound of claim 1, wherein $R_n$ is

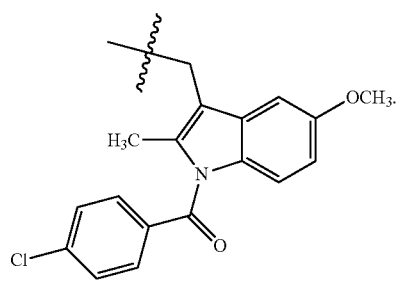 [SMILES: *Cc1c(C)n(C(=O)c2ccc(Cl)cc2)c2ccc(OC)cc12]

4. The compound of claim 1, wherein $R_n$ is

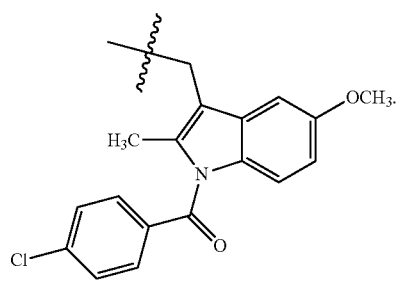 [SMILES: *Cc1c(C)n(C(=O)c2ccc(Cl)cc2)c2ccc(OC)cc12]

5. The compound of claim 1, wherein W1 and W2 are each NH.
6. The compound of claim 1, wherein m is 0.
7. The compound of claim 1, wherein L is —S—S—.
8. The compound of claim 1, wherein L is —O—.
9. The compound of claim 1, wherein L is NR3.
10. The compound of claim 1, wherein two of n, o, p, and q are each 1.
11. The compound of claim 1, wherein r is 2, s is 6, and t is 1.
12. The compound of claim 1, wherein r is 3, s is 5, and t is 1.
13. The compound of claim 1, wherein n, o, p, and q are each 1.
14. The compound of claim 1, wherein W1 and W2 are each NH; m is 0; n and o are each 1; and p and q are each 0.
15. The compound of claim 12, wherein W1 and W2 are each NH; m is 0; n and o are each 1; and p and q are each 0.
16. The compound of claim 13, wherein W1 and W2 are each NH; m is 0; n and o are each 1; and p and q are each 0.
17. The compound of claim 1, wherein W1 and W2 are each NH; m is 1; n, o, p, and q are each 1; and L is —O—.
18. The compound of claim 1, wherein W1 and W2 are each NH; m is 1; n, o, p, and q are each 1; and L is NR3.
19. The compound of claim 1, wherein W1 and W2 are each NH; m is 1; n, o, p, and q are each 1; and L is —S—S—.
20. The compound of claim 1, wherein the compound is

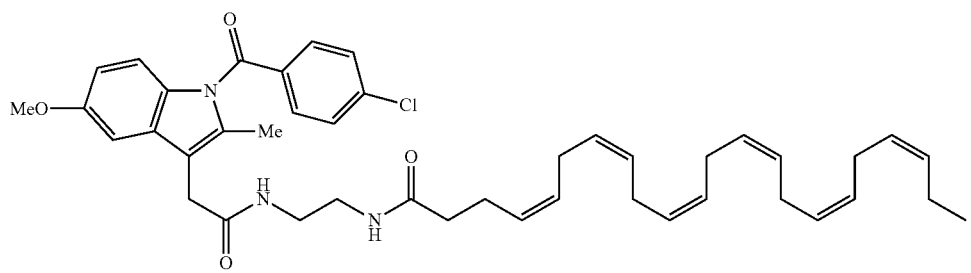 [SMILES: CC/C=C\C/C=C\C/C=C\C/C=C\C/C=C\C/C=C\CCC(=O)NCCNC(=O)Cc1c(C)n(C(=O)c2ccc(Cl)cc2)c2ccc(OC)cc12]

(4Z,7Z,10Z,13Z,16Z,19Z)—N-(2-(2-(1-(4-chlorobenzoyl)-5-methoxy-2-methyl-1H-indol-3-yl)acetamido)ethyl)docosa-4,7,10,13,16,19-hexaenamide (I-11).

21. The compound of claim 1, wherein the compound is

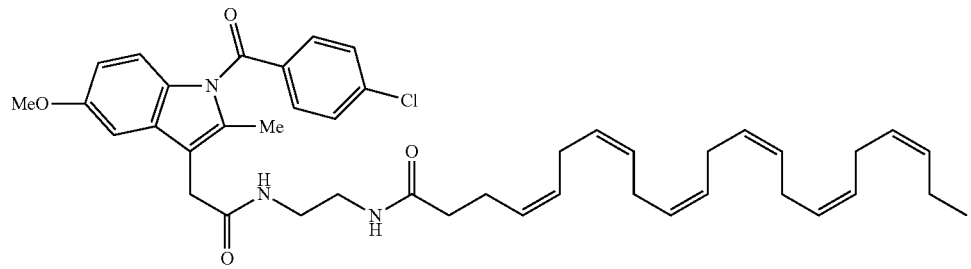 [SMILES: CC/C=C\C/C=C\C/C=C\C/C=C\C/C=C\C/C=C\CCC(=O)NCCNC(=O)Cc1c(C)n(C(=O)c2ccc(Cl)cc2)c2ccc(OC)cc12]

(5Z,8Z,11Z,14Z,17Z)—N-(2-(2-(1-(4-chlorobenzoyl)-5-methoxy-2-methyl-1H-indol-3-yl)acetamido)ethyl)icosa-5,8,11,14,17-pentaenamide (I-12).

22. The compound of claim 1, wherein the compound is

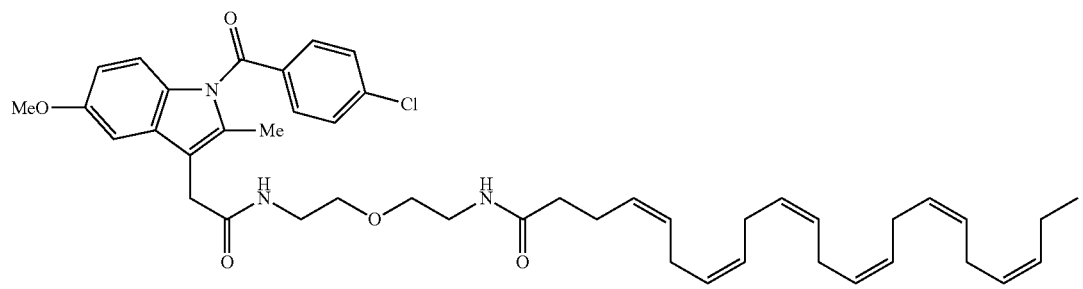 [SMILES: CC/C=C\C/C=C\C/C=C\C/C=C\C/C=C\C/C=C\CCC(=O)NCCOCCNC(=O)Cc1c(C)n(C(=O)c2ccc(Cl)cc2)c2ccc(OC)cc12]

4Z,7Z,10Z,13Z,16Z,19Z)—N-(2-(2-(2-(1-(4-chlorobenzoyl)-5-methoxy-2-methyl-1H-indol-3-yl)acetamido)ethoxy)ethyl)docosa-4,7,10,13,16,19-hexaenamide (I-13).

23. The compound of claim 1, wherein the compound is

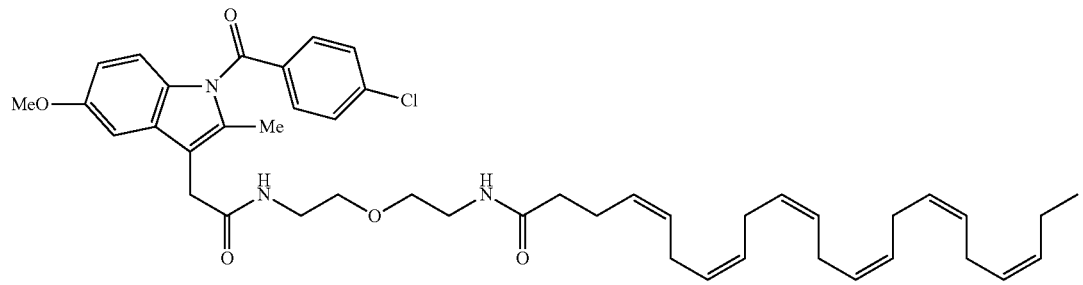 [SMILES: CC/C=C\C/C=C\C/C=C\C/C=C\C/C=C\C/C=C\CCC(=O)NCCOCCNC(=O)Cc1c(C)n(C(=O)c2ccc(Cl)cc2)c2ccc(OC)cc12]

(4Z,7Z,10Z,13Z,16Z,19Z)—N-(2-((2-(2-(1-(4-chlorobenzoyl)-5-methoxy-2-methyl-1H-indol-3-yl)acetamido)ethyl)(methyl)amino)ethyl)docosa-4,7,10,13,16,19-hexaenamide (I-14).

24. The compound of claim 1, wherein the compound is

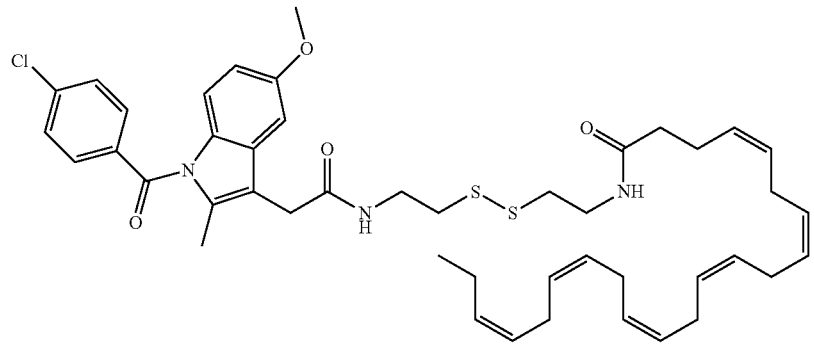 [SMILES: CC/C=C\C/C=C\C/C=C\C/C=C\C/C=C\C/C=C\CCC(=O)NCCSSCCNC(=O)Cc1c(C)n(C(=O)c2ccc(Cl)cc2)c2ccc(OC)cc12]

(4Z,7Z,10Z,13Z,16Z,19Z)—N-(2-(2-(2-(2-(1-(4-chlorobenzoyl)-5-methoxy-2-methyl-1H-indol-3-yl)acetamido)ethyl)disulfanyl)ethyl)docosa-4,7,10,13,16,19-hexaenamide (I-15).

25. The compound of claim 1, wherein the compound is

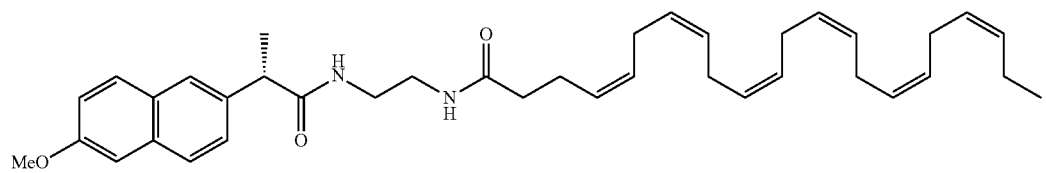 [SMILES: CC/C=C\C/C=C\C/C=C\C/C=C\C/C=C\C/C=C\CCC(=O)NCCNC(=O)[C@@H](C)c1ccc2cc(OC)ccc2c1]

(S,4Z,7Z,10Z,13Z,16Z,19Z)—N-(2-(2-(6-methoxynaphthalen-2-yl)propanamido)ethyl)docosa-4,7,10,13,16,19-hexaenamide (I-7).

26. The compound of claim 1, wherein the compound is

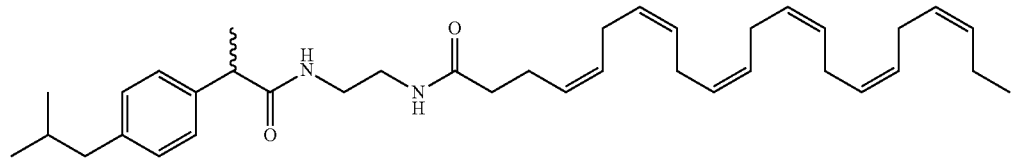 [SMILES: CC/C=C\C/C=C\C/C=C\C/C=C\C/C=C\C/C=C\CCC(=O)NCCNC(=O)C(C)c1ccc(CC(C)C)cc1]

(4Z,7Z,10Z,13Z,16Z,19Z)—N-(2-(2-(4-isobutylphenyl)propanamido)ethyl)docosa-4,7,10,13,16,19-hexaenamide (I-1).

27. A pharmaceutical composition comprising the compound of any one of claims 1-4 and 6-17 and a pharmaceutically acceptable carrier.

* * * * *